United States Patent [19]

Link

[11] Patent Number: 4,697,596
[45] Date of Patent: Oct. 6, 1987

[54] TECHNIQUES FOR OBTAINING INFORMATION ASSOCIATED WITH AN INDIVIDUAL'S BLOOD PRESSURE INCLUDING SPECIFICALLY A STAT MODE TECHNIQUE

[75] Inventor: William T. Link, Berkeley, Calif.

[73] Assignee: Baxter Travenol Laboratories, Inc., Deerfield, Ill.

[21] Appl. No.: 930,238

[22] Filed: Nov. 13, 1986

Related U.S. Application Data

[60] Division of Ser. No. 868,313, May 28, 1986, Pat. No. 4,664,126, which is a continuation-in-part of Ser. No. 684,592, Dec. 21, 1984, abandoned, which is a continuation-in-part of Ser. No. 622,213, Jun. 19, 1984, abandoned, and Ser. No. 622,080, Jun. 19, 1984, abandoned.

[51] Int. Cl.$^4$ .............................................. A61B 5/02
[52] U.S. Cl. ...................................... 128/681; 128/677
[58] Field of Search ................ 128/672, 677, 680–683, 128/687–688

[56] References Cited

U.S. PATENT DOCUMENTS

| | | | |
|---|---|---|---|
| 3,878,833 | 4/1975 | Arneson et al. | 128/681 |
| 3,903,872 | 9/1975 | Link | 128/681 |
| 4,009,709 | 3/1977 | Link et al. | 128/681 |
| 4,074,711 | 2/1978 | Link et al. | 128/681 |
| 4,137,907 | 2/1979 | Jansen et al. | 128/681 |
| 4,140,110 | 2/1979 | Jansen et al. | 128/681 |
| 4,144,879 | 3/1979 | Nakayama et al. | 128/680 |
| 4,154,238 | 5/1979 | Link | 128/681 |
| 4,174,707 | 11/1979 | Link et al. | 128/681 |
| 4,177,801 | 12/1979 | Grangirard et al. | 128/681 |
| 4,271,843 | 6/1981 | Flynn | 128/681 |
| 4,349,034 | 9/1982 | Ramsey, III | 128/681 |
| 4,360,029 | 11/1982 | Ramsey, III | 128/681 |
| 4,367,751 | 1/1983 | Link et al. | 128/681 X |
| 4,408,614 | 10/1983 | Weaver | 128/680 |
| 4,461,266 | 7/1984 | Hood, Jr. et al. | 128/677 X |
| 4,484,584 | 11/1984 | Uemura | 128/680 |

FOREIGN PATENT DOCUMENTS 2092309   8/1982   United Kingdom ............... 128/672

OTHER PUBLICATIONS

Link, Norse Systems Automatic Electronic Blood Pressure Monitor Using Waveform Analysis Oscillometry, 8-1974, pp. 1-10.

Primary Examiner—Henry J. Recla
Assistant Examiner—Angela D. Sykes
Attorney, Agent, or Firm—Flehr, Hohbach, Test, Albritton & Herbert

[57] ABSTRACT

Techniques for determining different parameters associated with an individual's blood pressure in a non-invasive manner are disclosed herein. These techniques include (1) generating a blood pressure waveform corresponding to the individual's actual waveform, whereby the mean pressure of the individual can be readily calculated, (2) generating a transformation curve unique to the patient from his diastolic and systolic pressures and his cuff pulses, (3) successively monitoring certain parameters of the patient's blood pressure including his systolic and diastolic pressures over closely spaced intervals of time without having to subject the patient to cuff pressures much greater than his diastolic pressure, other than initially or not at all utilizing what is referred to as a stat mode, and (4) measuring a patient's diastolic and systolic blood pressures at any given instance without ever having to subject the patient to cuff pressures much greater than his diastolic pressure.

10 Claims, 40 Drawing Figures

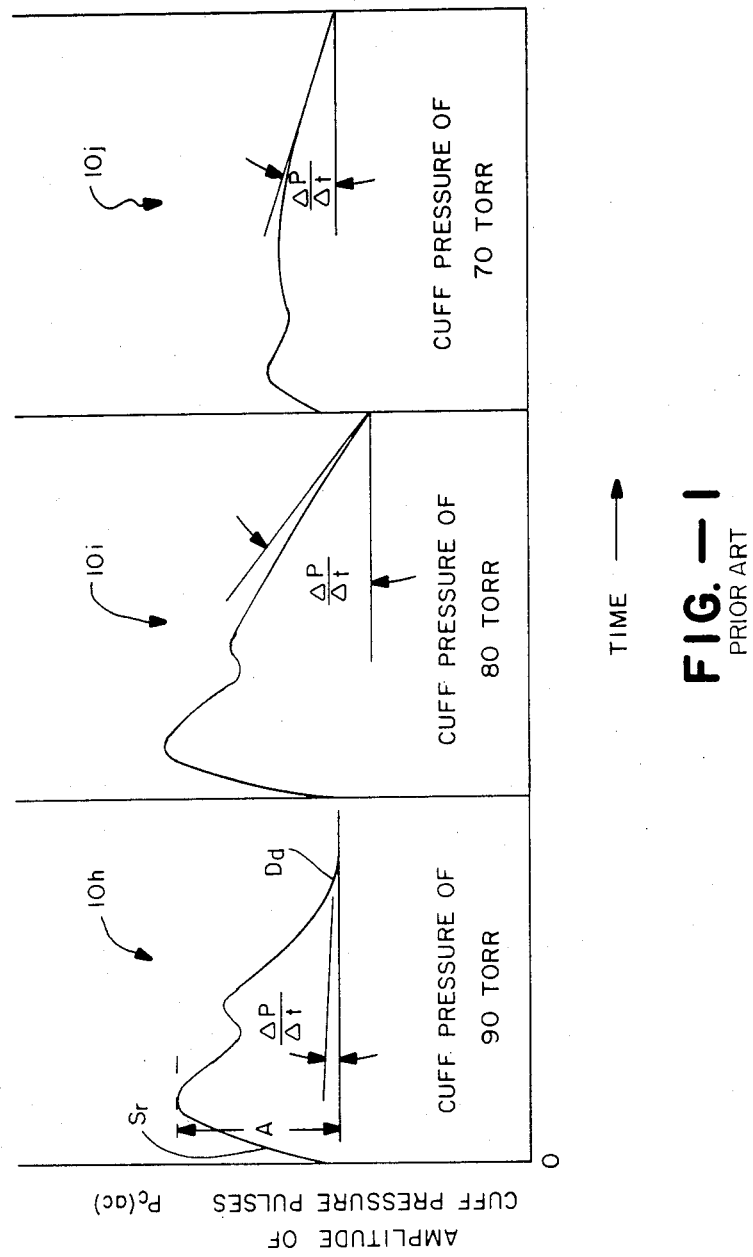

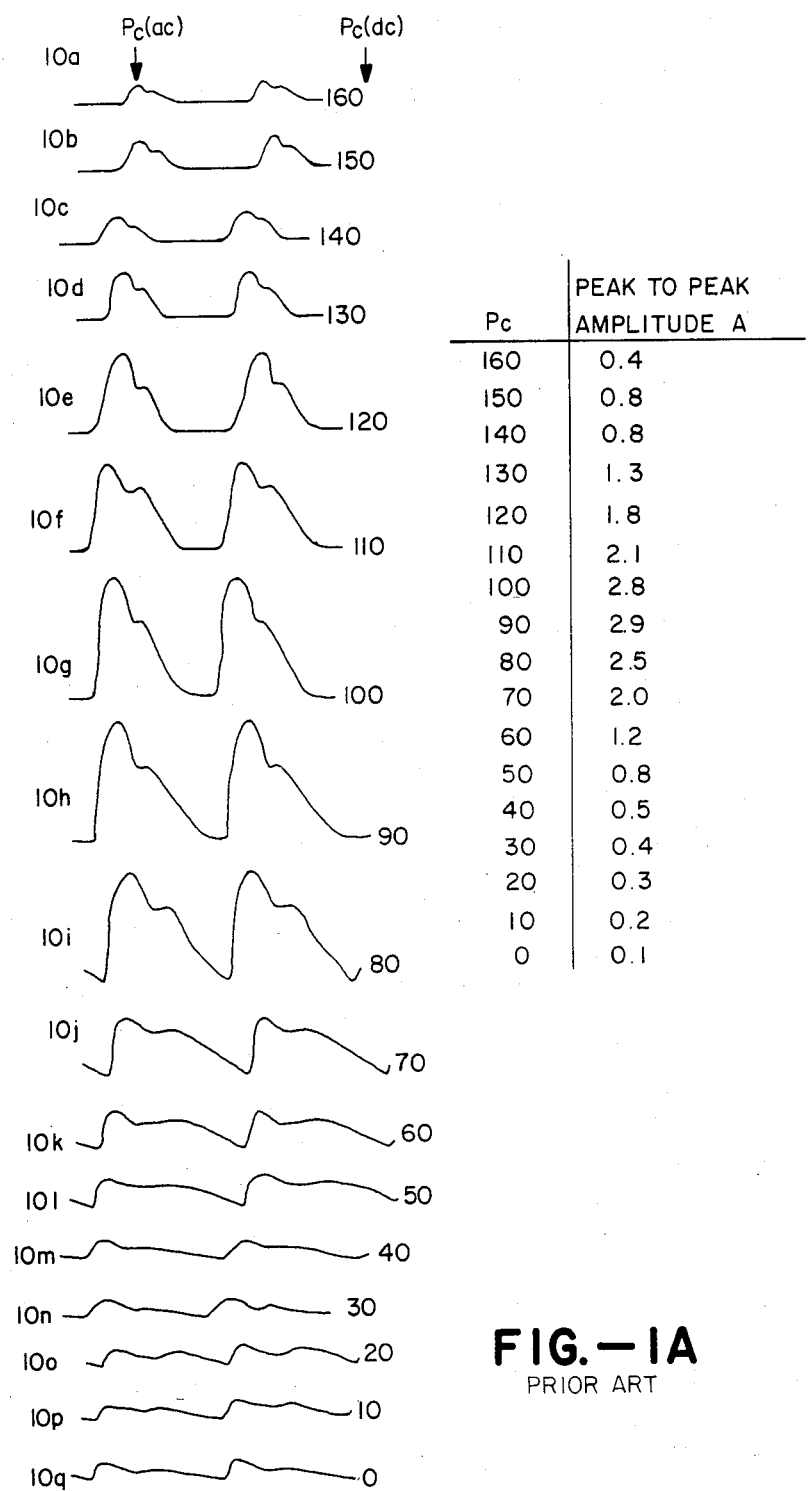
| $P_c$ | PEAK TO PEAK AMPLITUDE A |
|---|---|
| 160 | 0.4 |
| 150 | 0.8 |
| 140 | 0.8 |
| 130 | 1.3 |
| 120 | 1.8 |
| 110 | 2.1 |
| 100 | 2.8 |
| 90 | 2.9 |
| 80 | 2.5 |
| 70 | 2.0 |
| 60 | 1.2 |
| 50 | 0.8 |
| 40 | 0.5 |
| 30 | 0.4 |
| 20 | 0.3 |
| 10 | 0.2 |
| 0 | 0.1 |
FIG.—1A
PRIOR ART

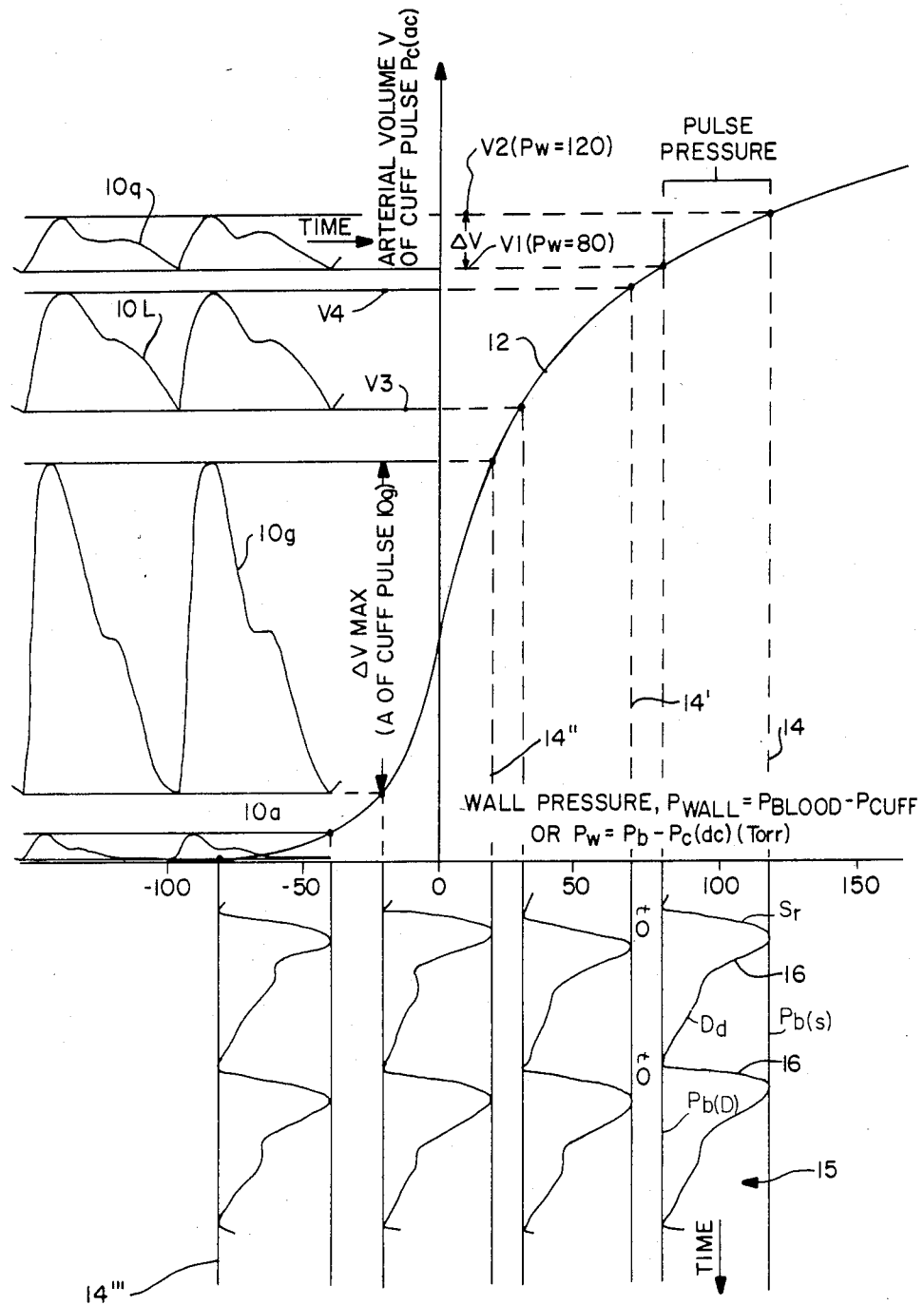
FIG.—2
PRIOR ART

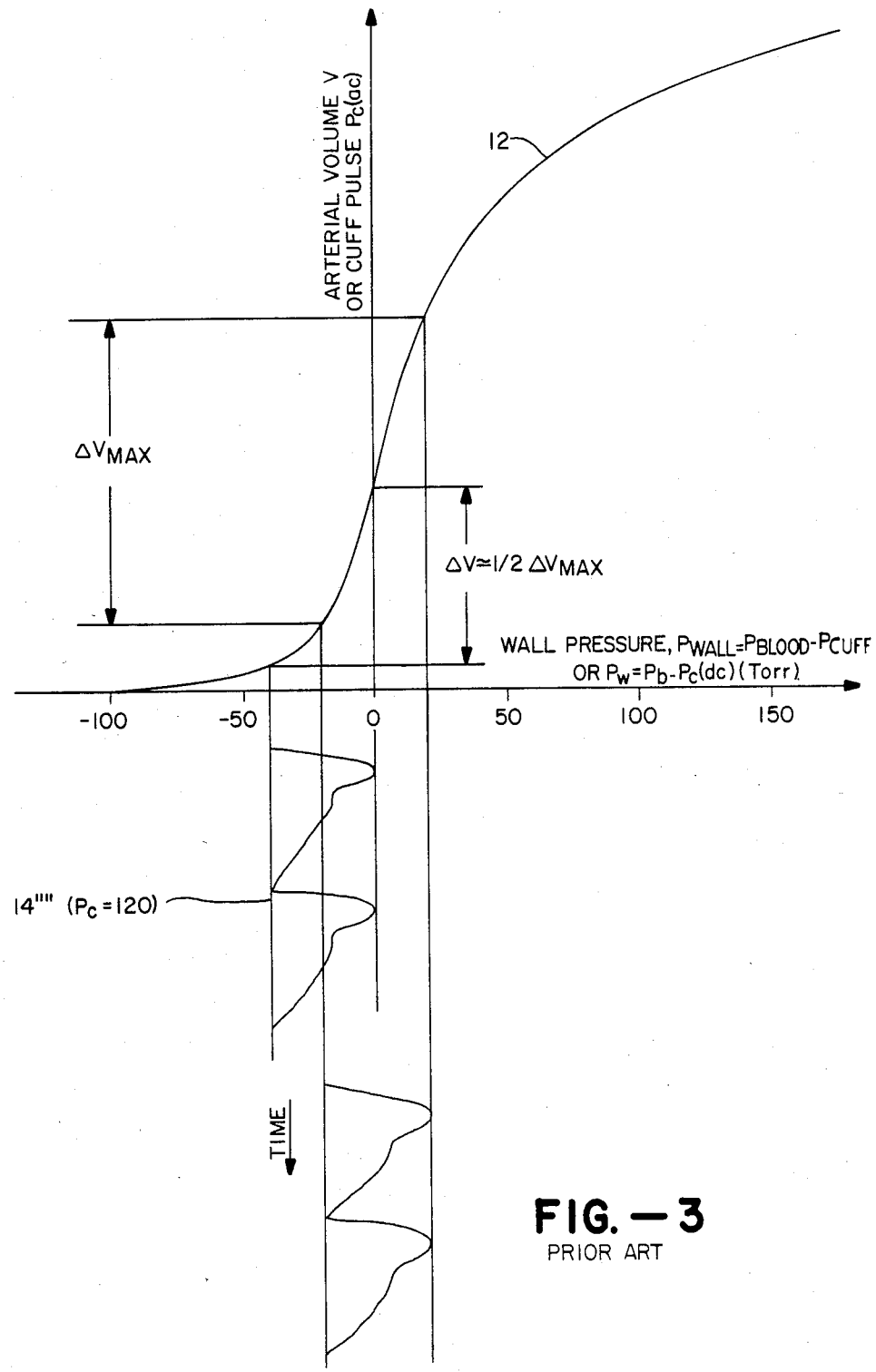
FIG.—3
PRIOR ART

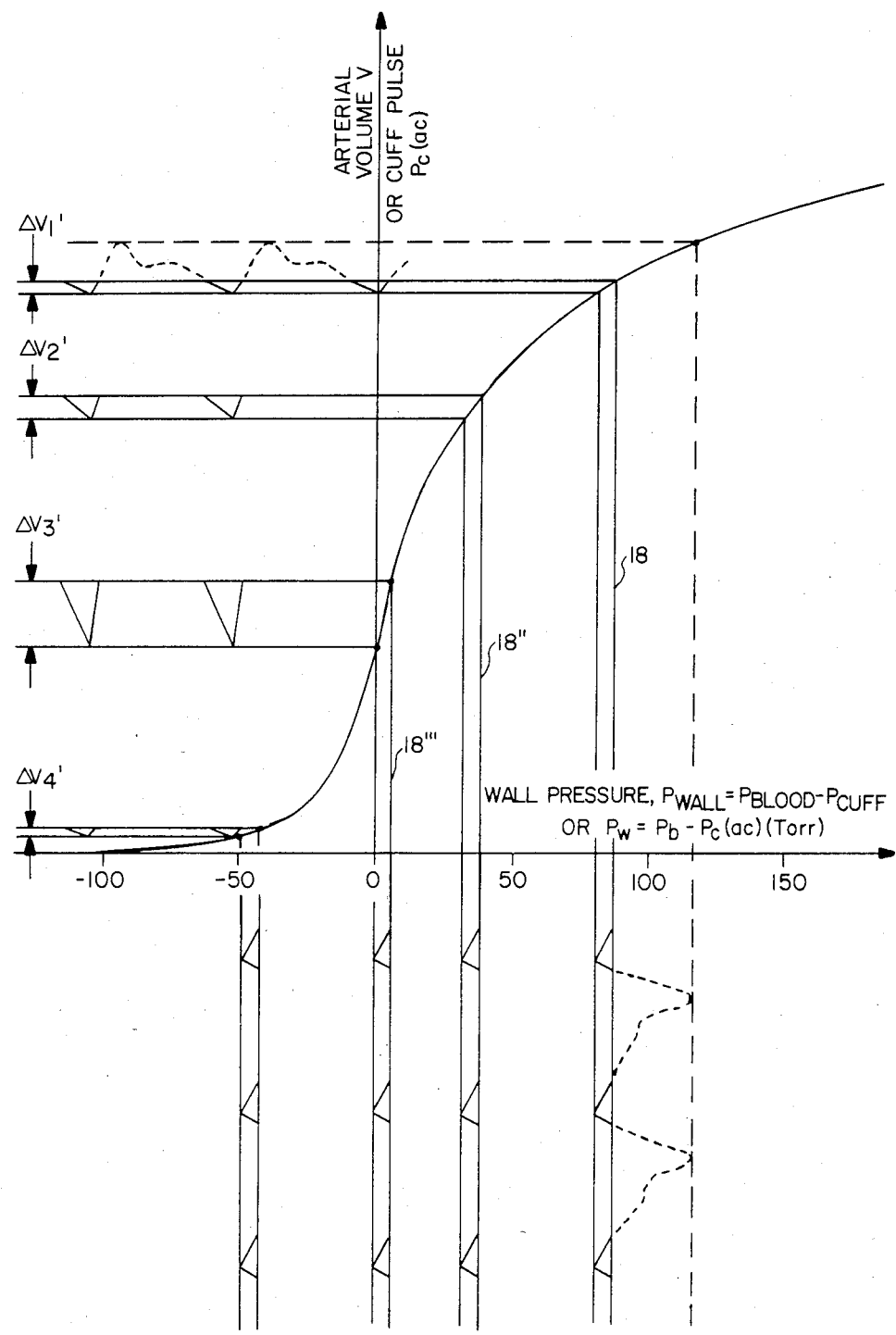
FIG.—4
PRIOR ART

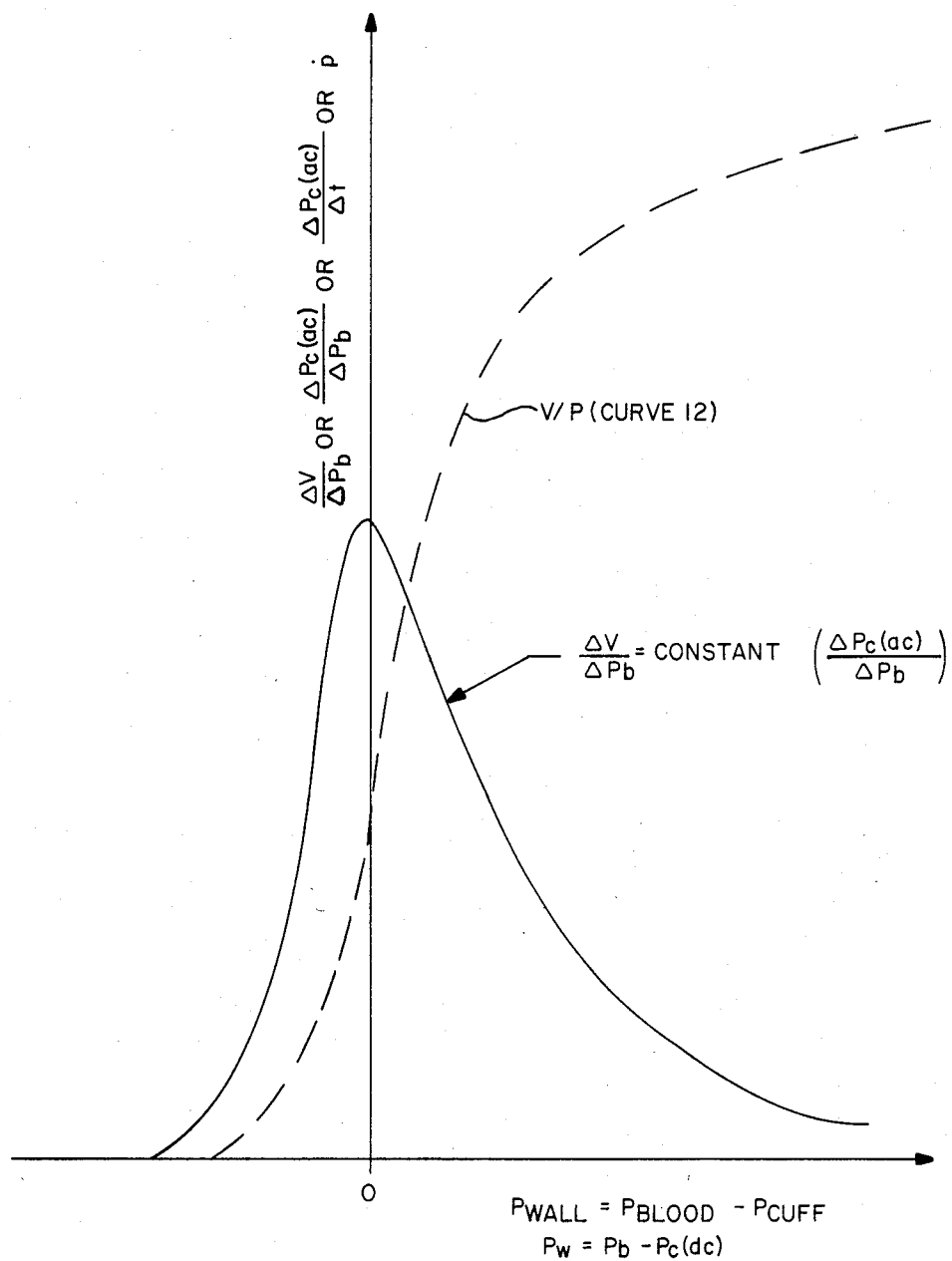
FIG. — 5
PRIOR ART

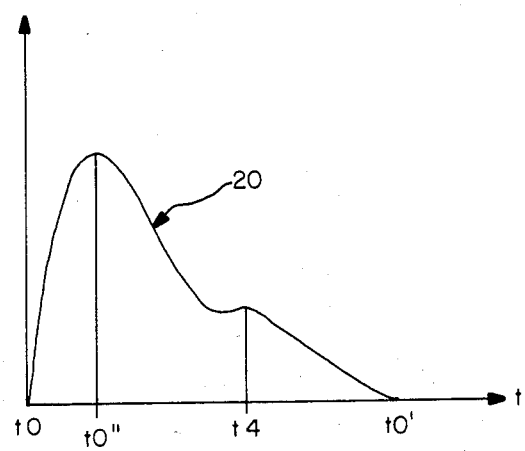
FIG.—6
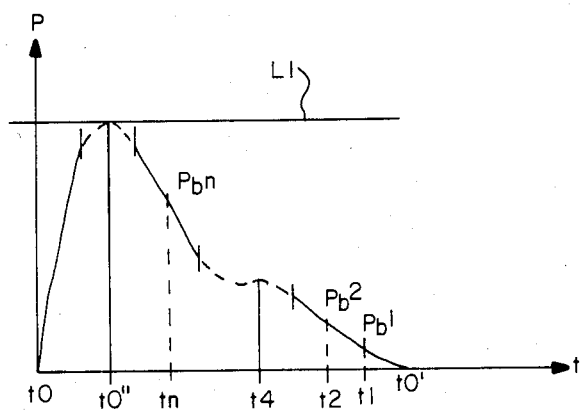
FIG.—7
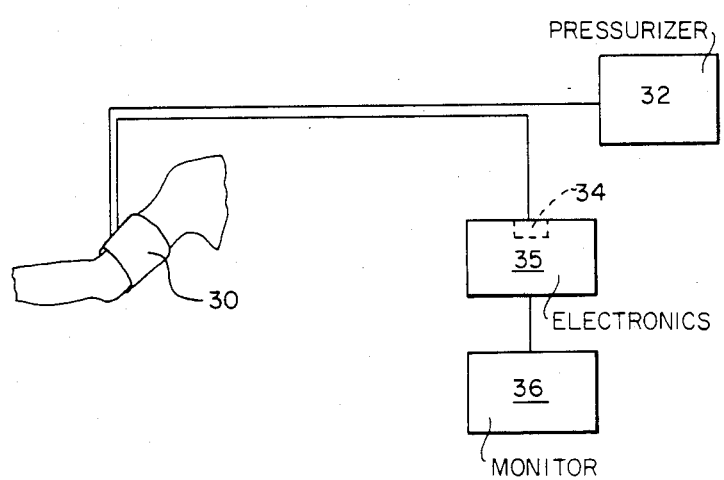
FIG.—10

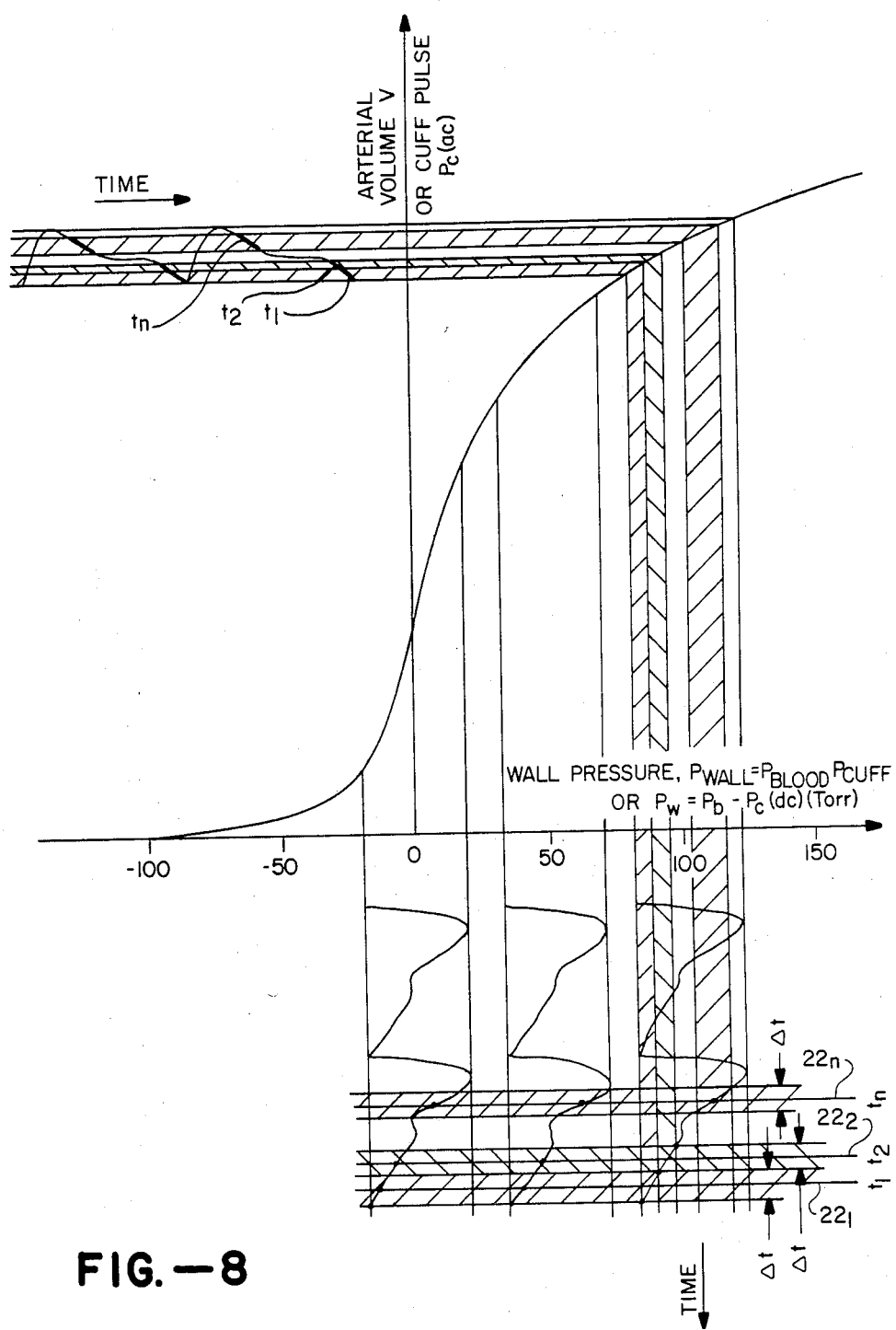
FIG.—8

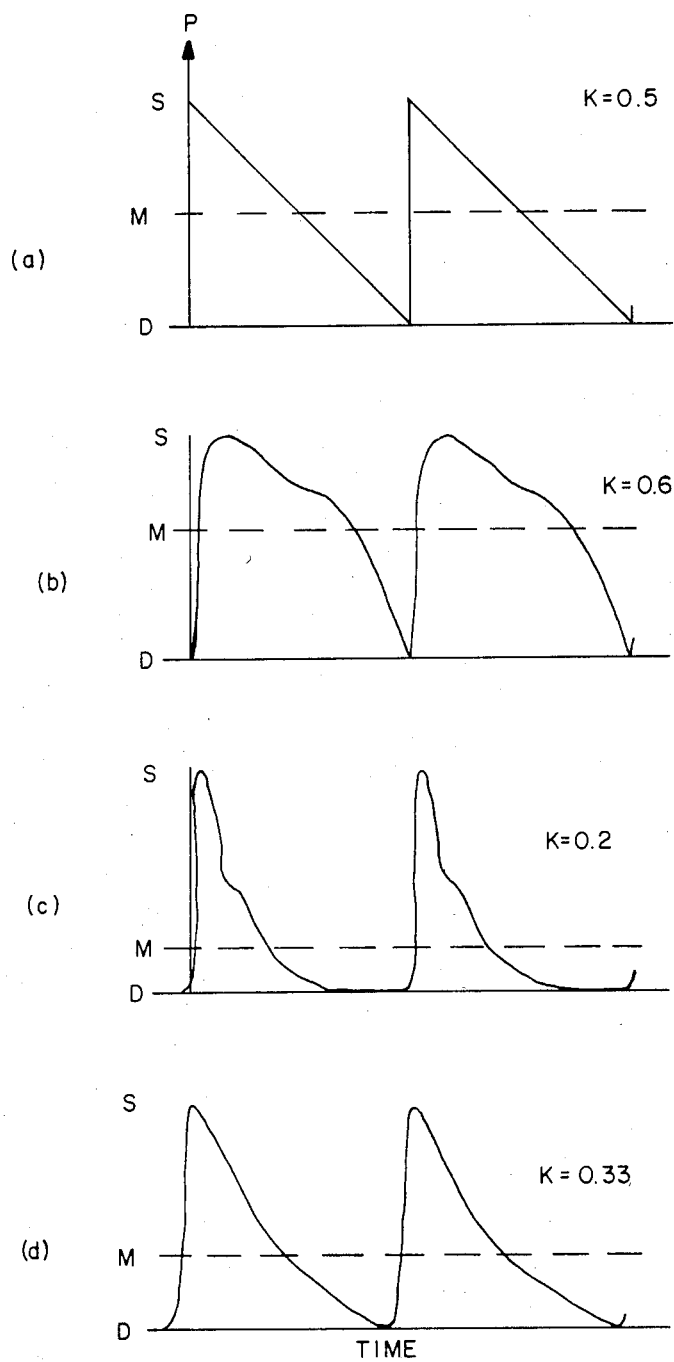
FIG.—9

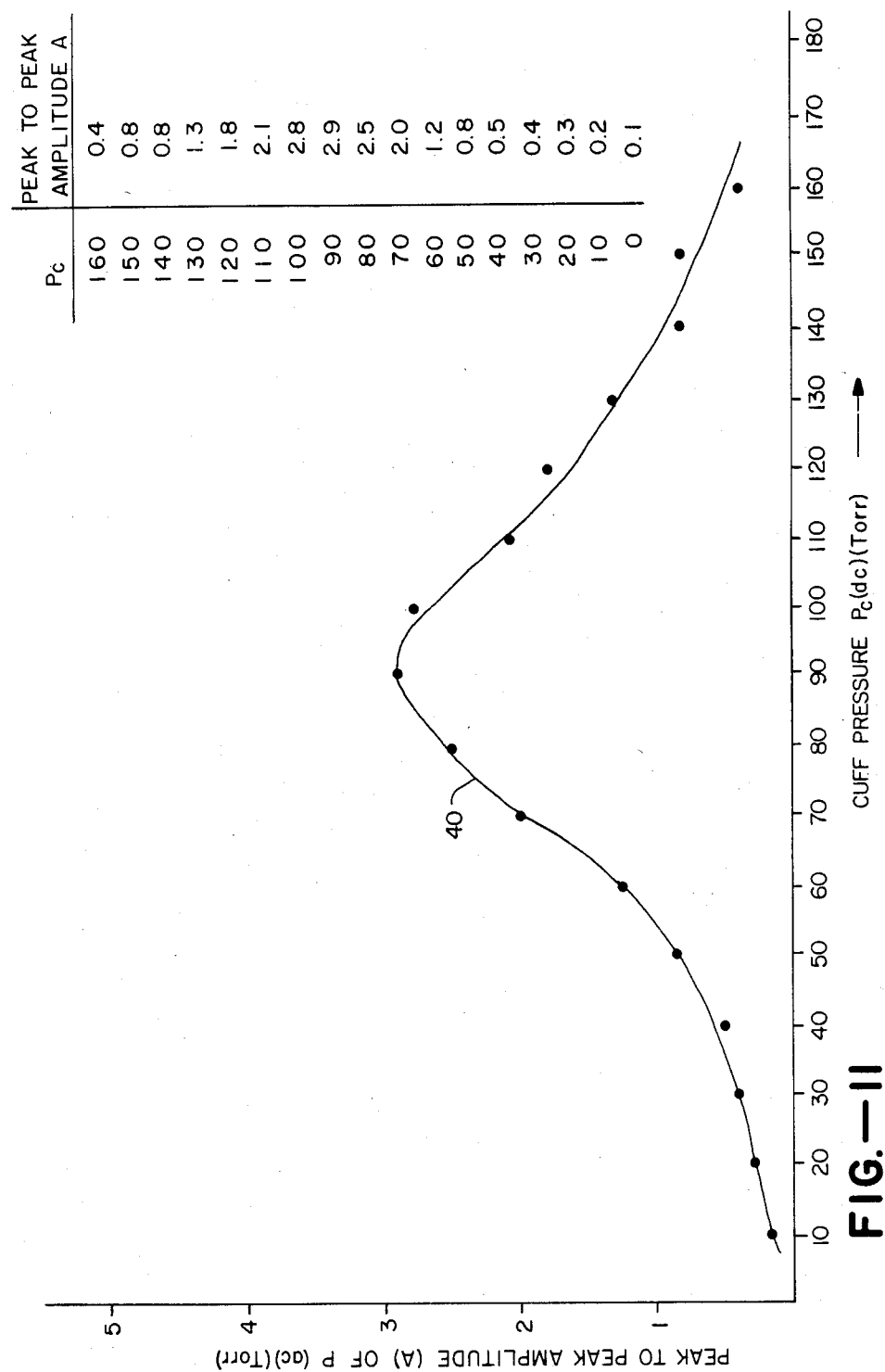
FIG.—11

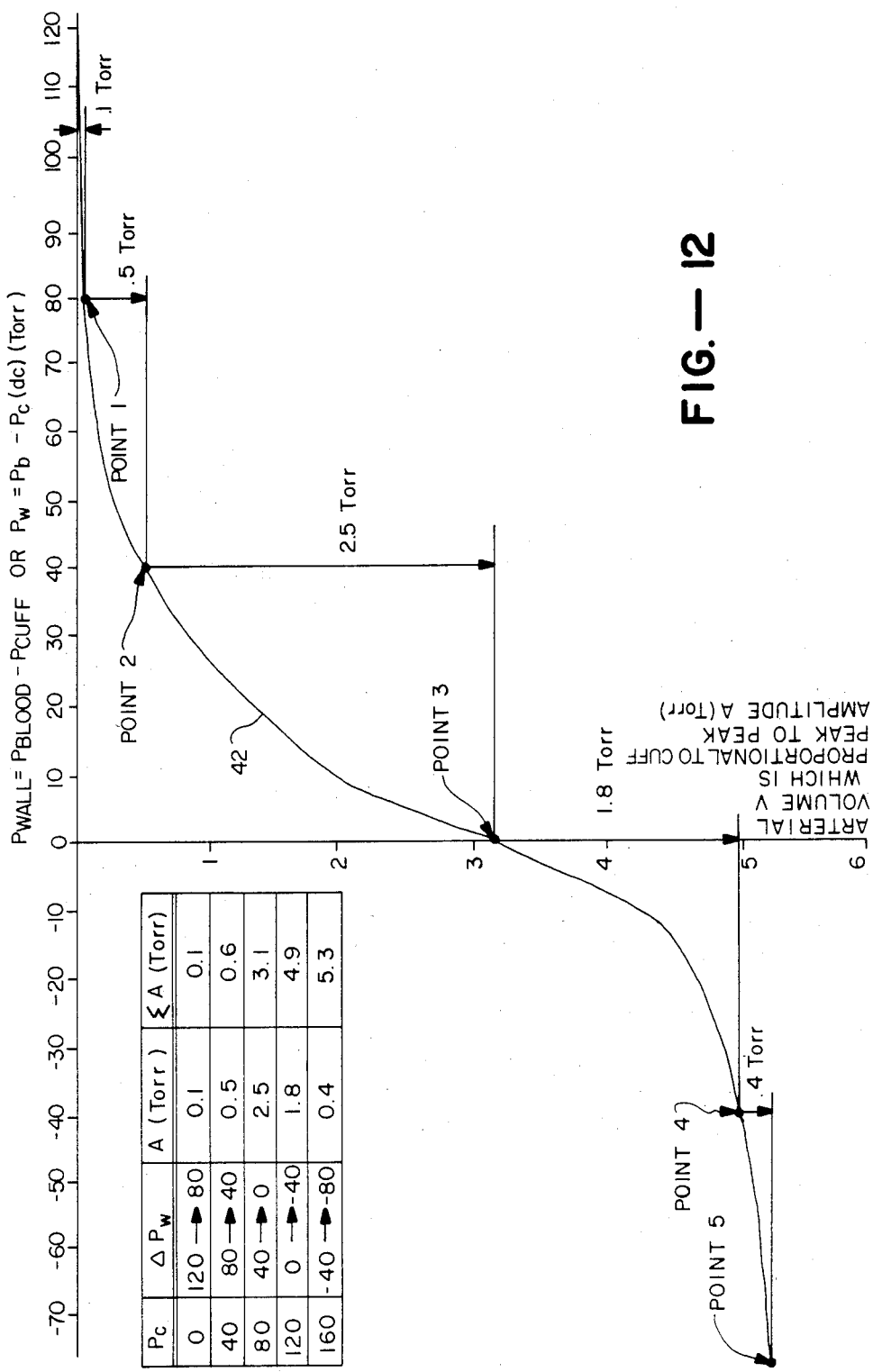
FIG.—12

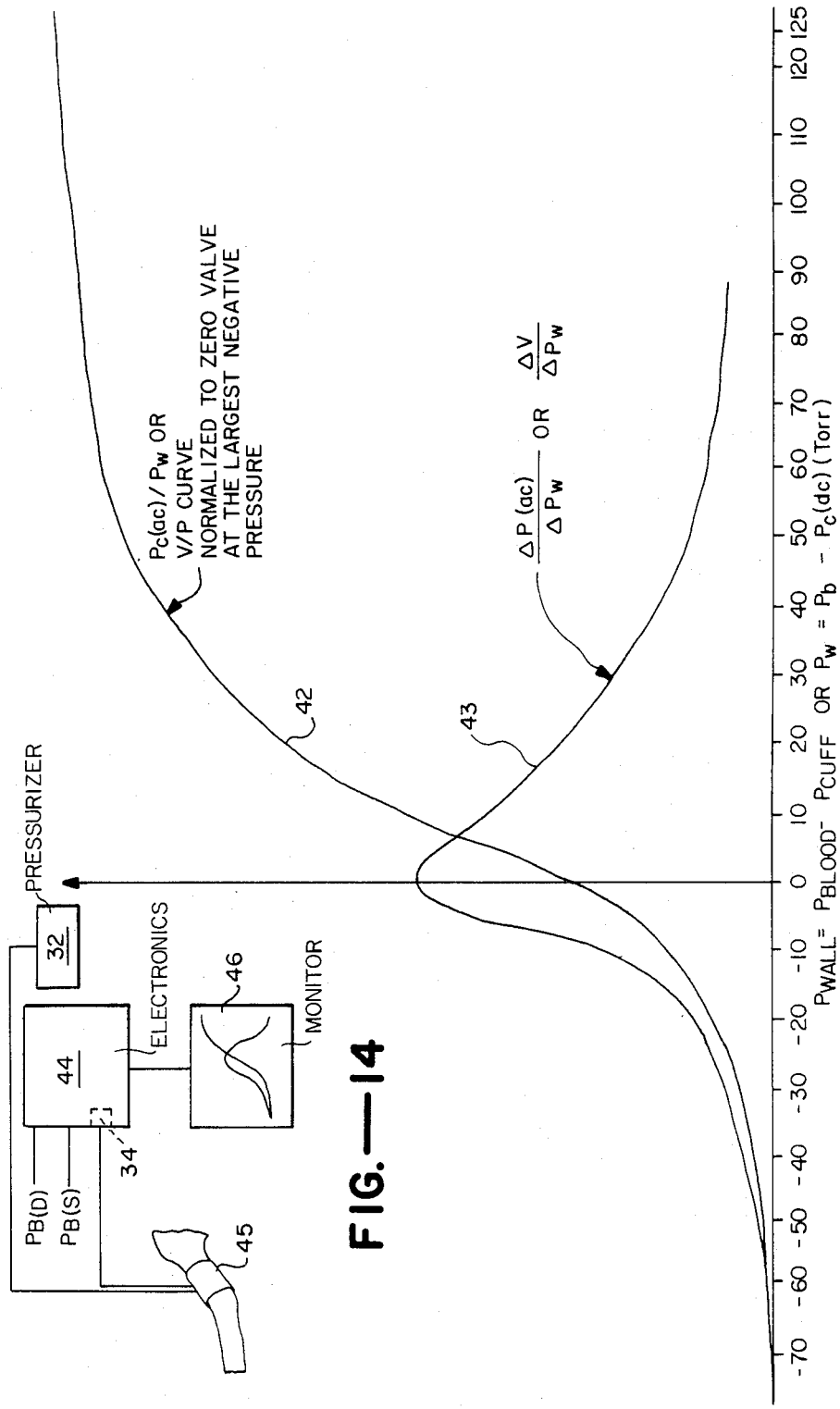
FIG.—13
FIG.—14

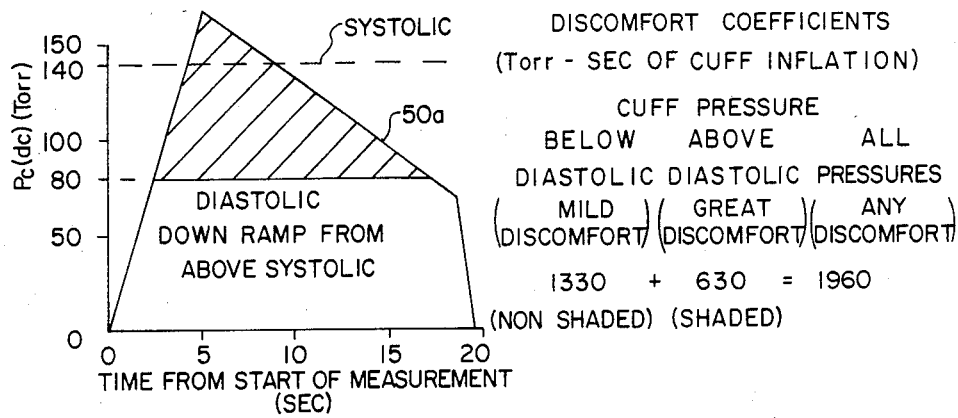
FIG.—15a
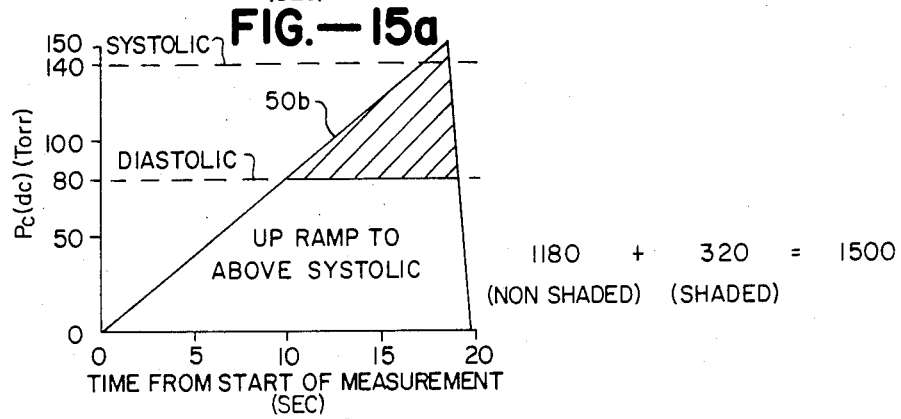
FIG.—15b
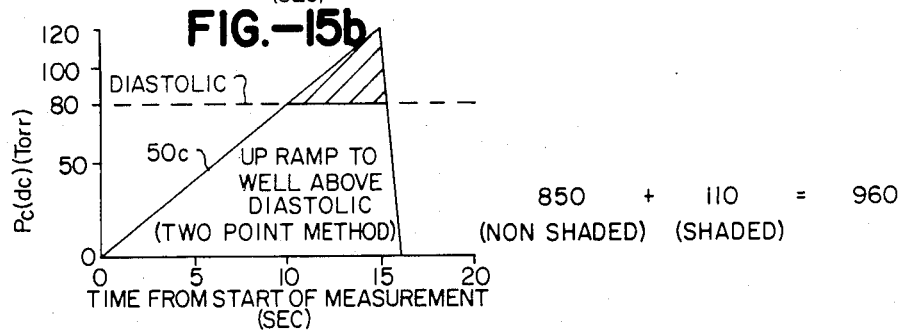
FIG.—15c
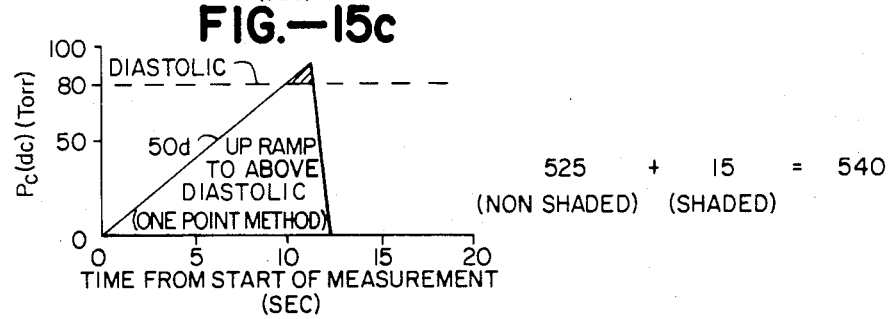
FIG.—15d

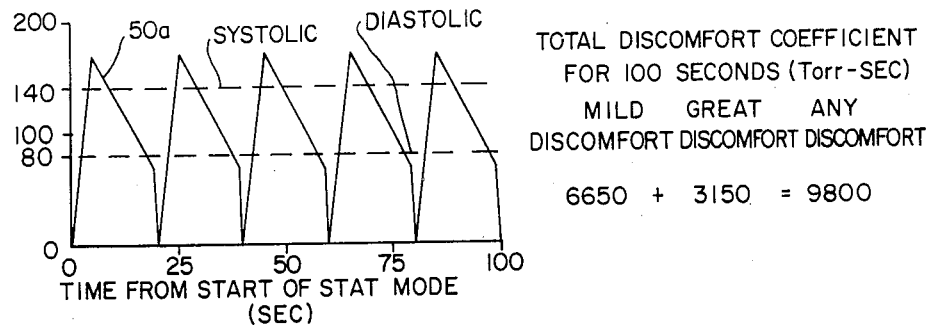
FIG.—16a
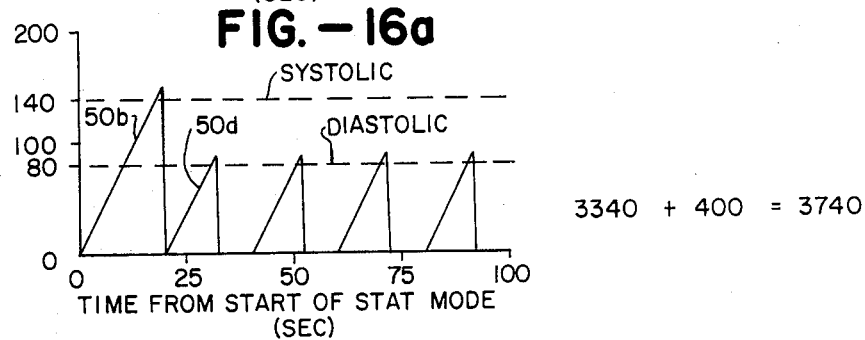
FIG.—16b
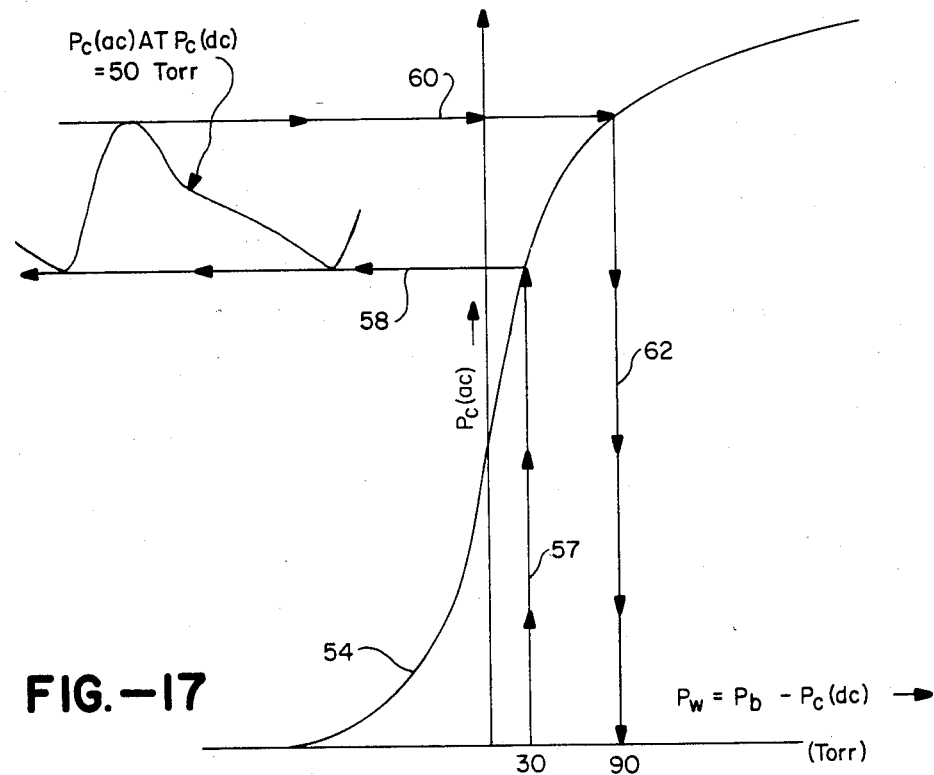
FIG.—17

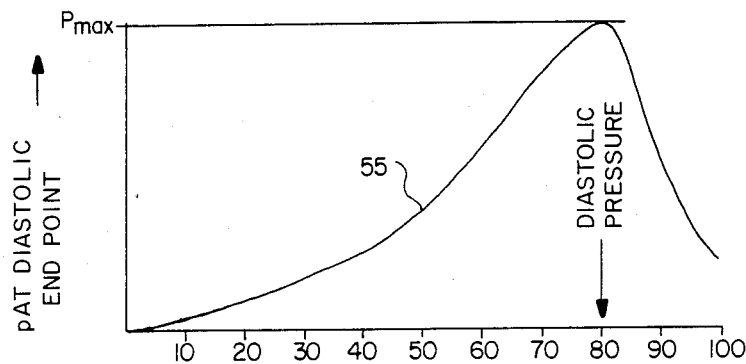
FIG.—18
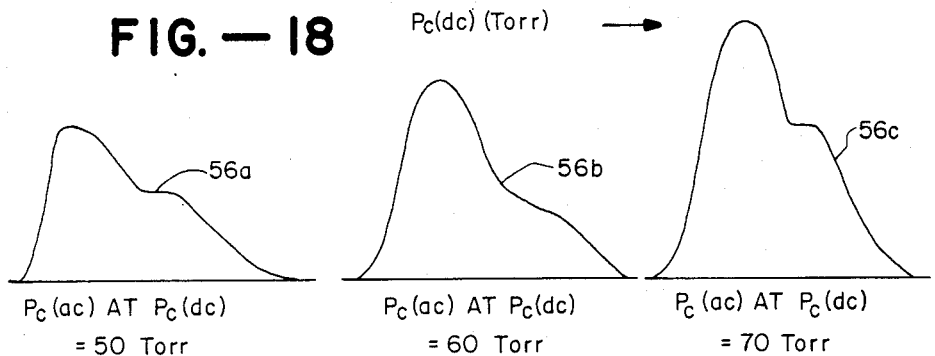
FIG.—19a    FIG.—19b    FIG.—19c
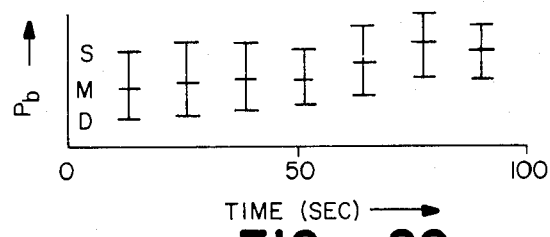
FIG.—20
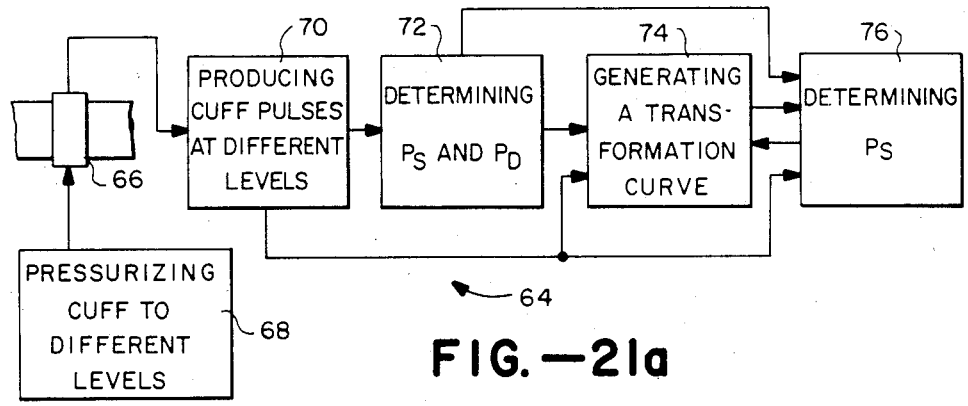
FIG.—21a

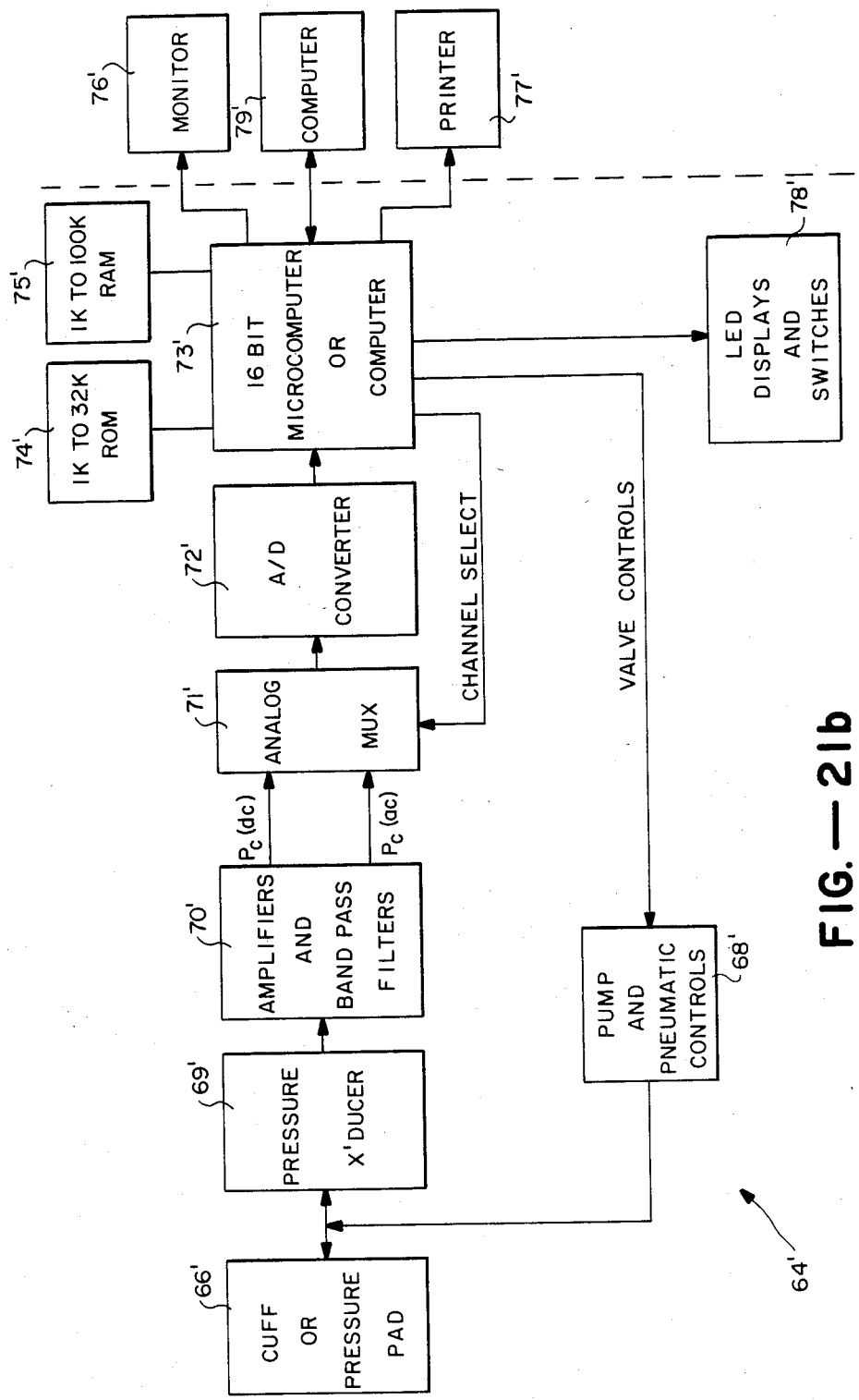
FIG.—21b

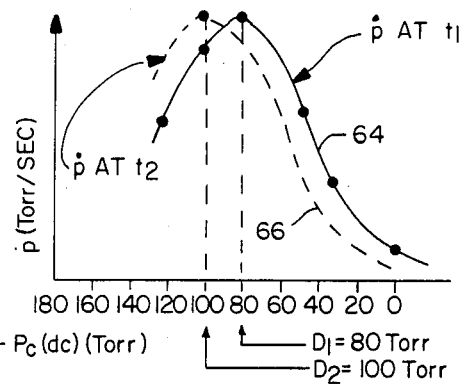
FIG.—22
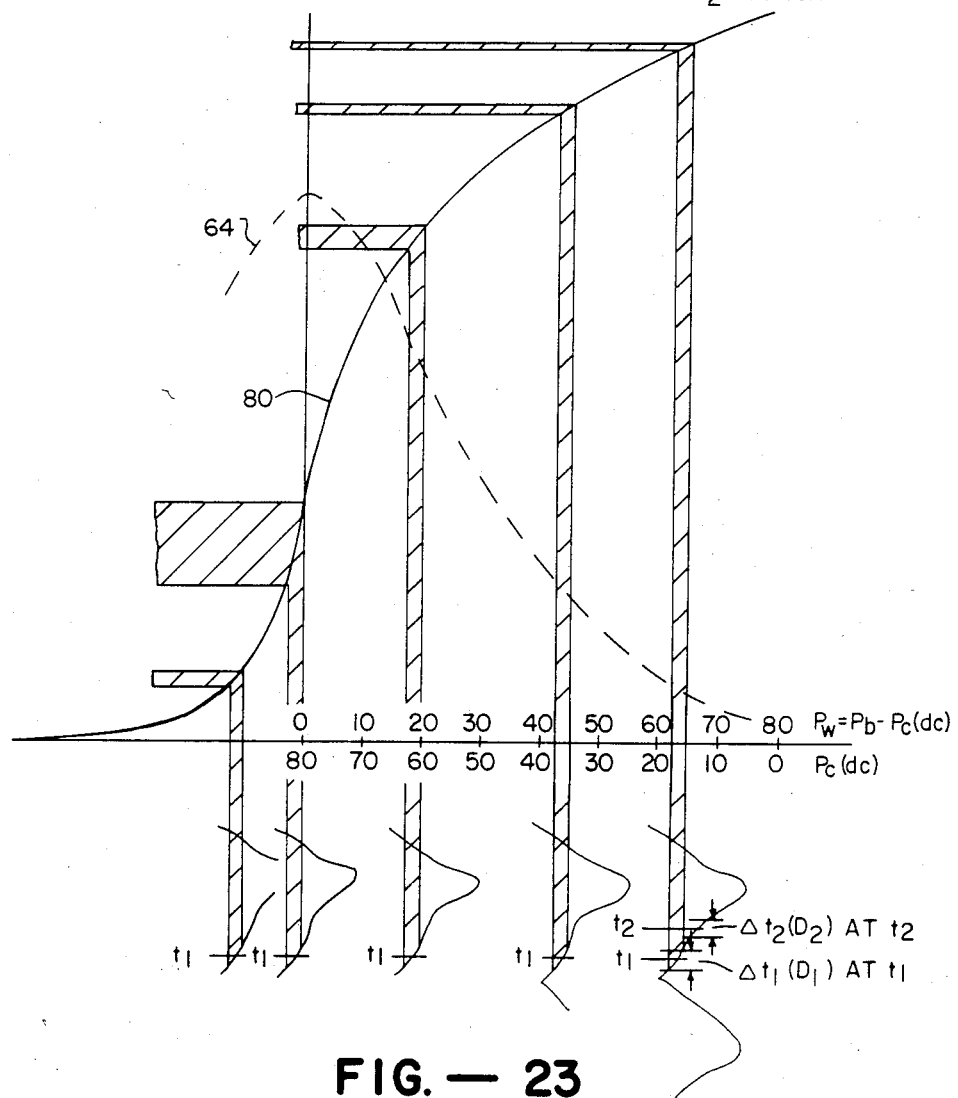
FIG.—23

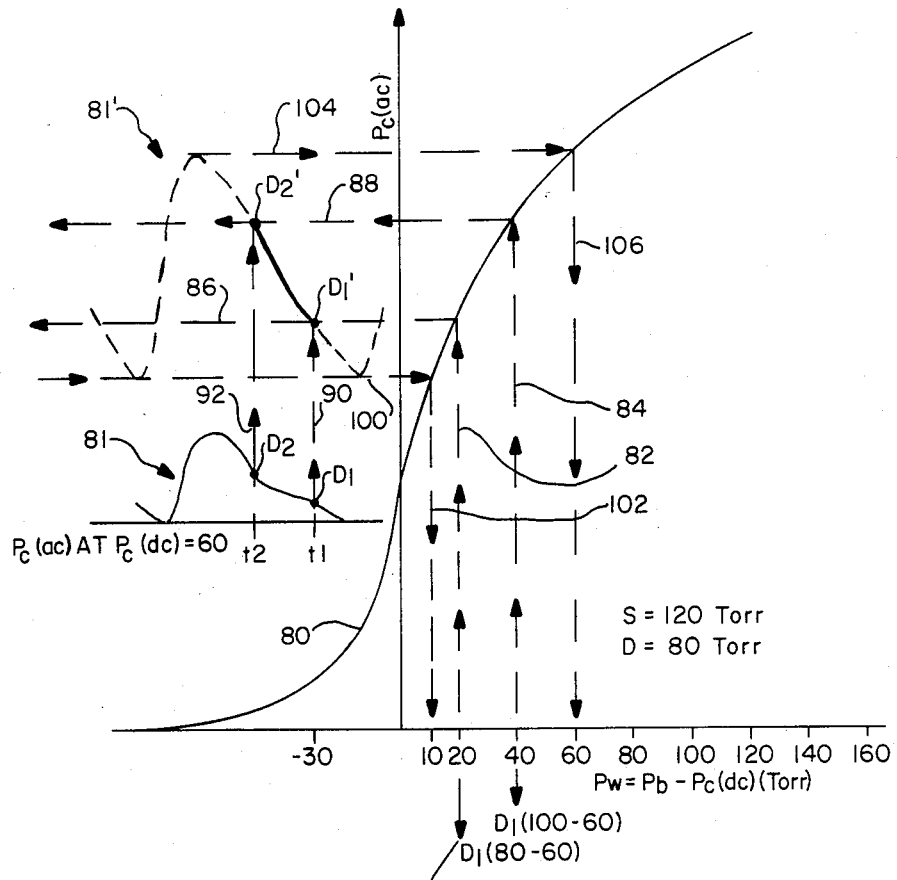
FIG.—24
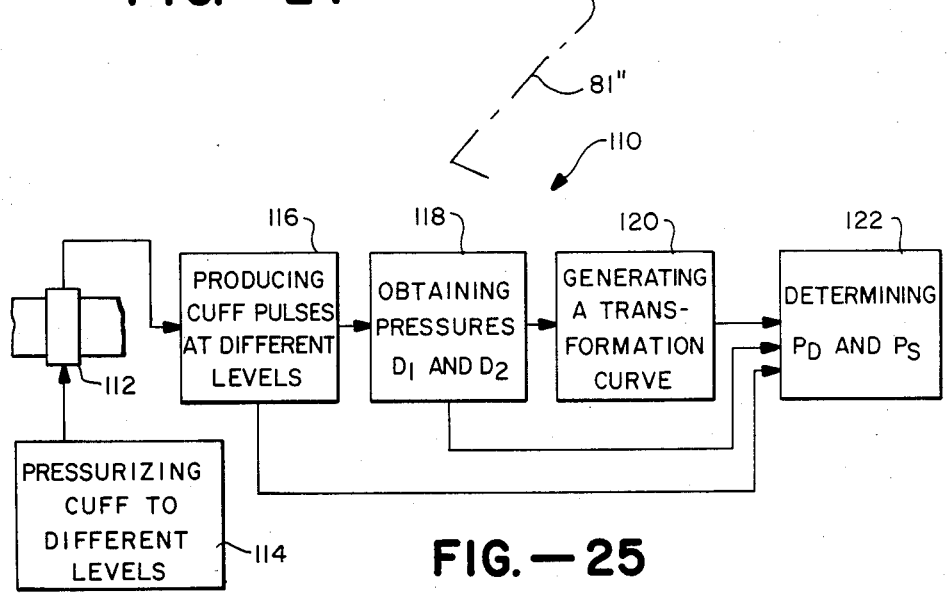
FIG.—25

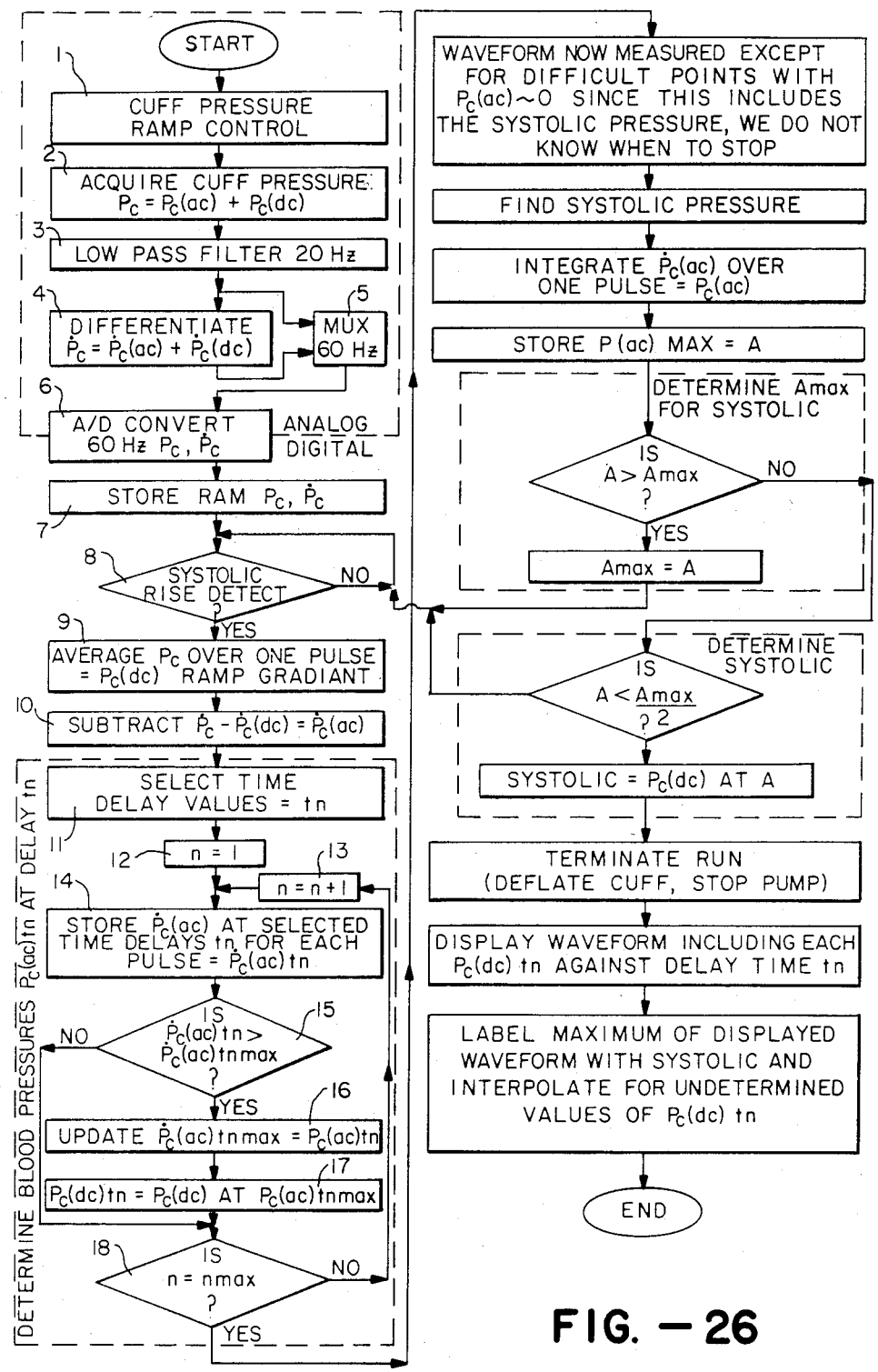
FIG. — 26

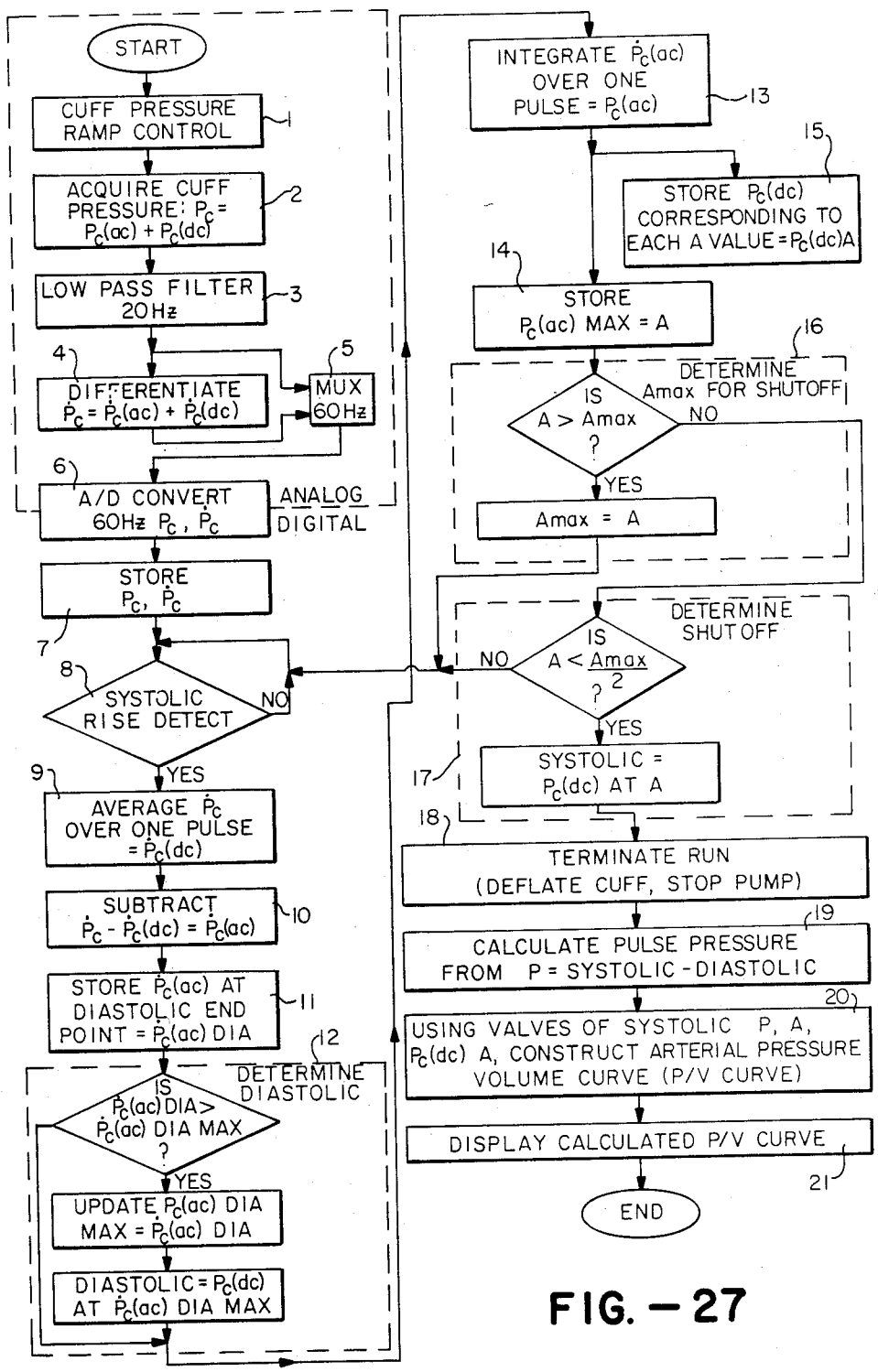
FIG. —27

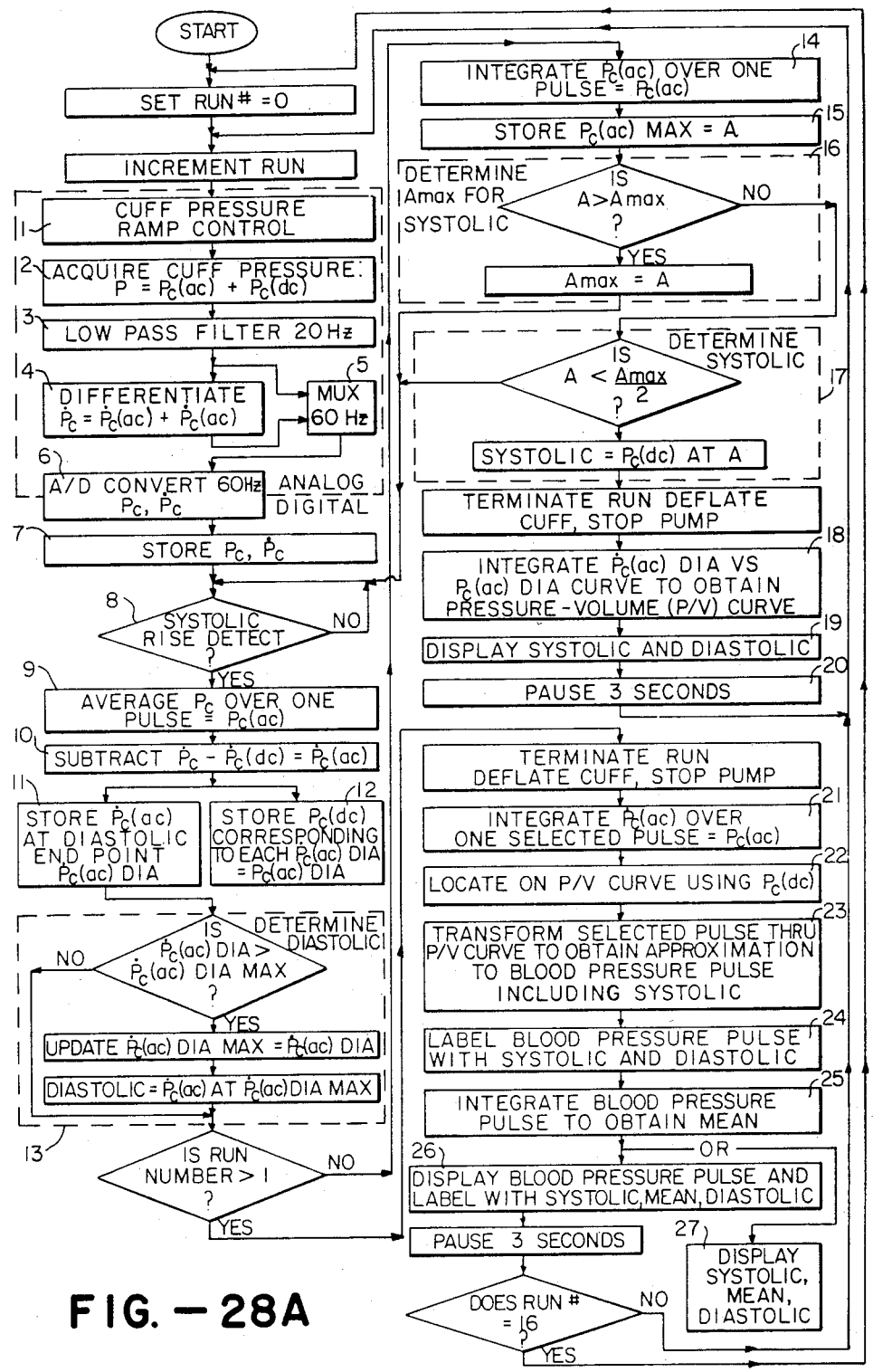
FIG.—28A

TECHNIQUES FOR OBTAINING INFORMATION ASSOCIATED WITH AN INDIVIDUAL'S BLOOD PRESSURE INCLUDING SPECIFICALLY A STAT MODE TECHNIQUE

BACKGROUND OF THE INVENTION

This is a division of application Ser. No. 868,313 filed May 28, 1986, now U.S. Pat. No. 4,664,126, which is a continuation-in-part of U.S. application Ser. No. 684,592 filed Dec. 21, 1984, abandoned, which, in turn is a continuation-in-part of U.S. patent application Ser. No. 622,213 and 622,080, both filed June 19, 1984 and now abandoned.

The present invention relates generally to blood pressure evaluation procedures and more particularly to non-invasive techniques for determining certain information associated with blood pressure.

The most reliable ways presently known for obtaining information relating to an individual's blood pressure require invasive procedures. Such procedures are not carried out routinely but only under extreme circumstances, for example during heart surgery. Under less critical conditions, blood pressure information including specifically an individual's systolic (maximum) and diastolic (minimum) blood pressures is obtained non-invasively. There are two well known non-invasive techniques presently being used today, one is commonly referred to as auscultation and the other is based on oscillometry. Both of these non-invasive techniques use the standard arm cuff which most people are familiar with. However, in the auscultatory method, the systolic and diastolic pressures are determined by listening to certain sounds (Korotkoff sounds) which occur as a result of the cuff first being pressurized and then depressurized whereas oscillometry actually measures changes in pressure in the cuff as a result of changes in blood pressure as the cuff is first pressurized and then depressurized.

As will be seen hereinafter, the various embodiments of the present invention are based on oscillometry. In order to more fully appreciate these embodiments, reference is made to applicant's own U.S. Pat. No. 3,903,872 (the Link patent) for obtaining blood pressure information non-invasively. This patent which is incorporated herein by reference describes, among other things, a way of obtaining the diastolic pressure of an individual in accordance with a technique which will be discussed detail hereinafter. In U.S. Pat. Nos. 4,009,709 and 4,074,711 (Link et al) which are also incorporated herein by reference, non-invasive techniques using oscillometry are disclosed for obtaining the systolic pressure of an individual. These techniques will also be discussed hereinafter.

While the various procedures described in the Link and Link et al patents just recited and other patents held by applicant are satisfactory for their intended purposes, it is an object of the present invention to provide additional uncomplicated and yet reliable techniques for obtaining different types of information relating to an individual's blood pressure.

SUMMARY OF THE INVENTION

A more specific object of the present invention is to provide a different uncomplicated and yet reliable technique for generating non-invasively a waveform closely approximating an individual's true blood pressure waveform which, heretofore, has been obtainable by invasive means only.

Another particular object of the present invention is to provide a new way for measuring and calculating the mean arterial pressure of an individual.

Another specific object of the present invention is to provide a new, uncomplicated and yet reliable technique for generating a transformation curve unique to a given patient.

Still another specific object of the present invention is to provide a technique for successively monitoring certain parameters of a patient's blood pressure including his systolic and diastolic pressures over closely spaced intervals of time without having to subject the patient to cuff pressures much greater than his diastolic pressure, other than initially (for purposes of calibration).

Yet another specific object of the present invention is to provide a technique for measuring a patient's diastolic and systolic blood pressures at any given instance without ever having to subject the patient to cuff pressures much greater than his diastolic pressure.

As will be described in more detail hereinafter, the objects just recited are achieved by means of oscillometry. In accordance with this technique, a suitably sized cuff, for example one which is 20 inches long and 5 inches wide, is positioned around the upper arm of an individual, a human being specifically or a mammal in general (hereinafter referred to as the patient) and initially pressurized to a certain minimum level. As will be seen hereinafter in accordance with one aspect of the present invention, this minimum level need not be much greater than the patient's diastolic pressure to obtain certain information about the patient's blood pressure including his diastolic and systolic pressures. However, heretofore, in order to measure these pressure values and obtain other information, it was necessary to subject the patient to a minimum cuff pressure greater than the patient's systolic pressure, for example 180 Torr. It is assumed that this latter cuff pressure will cause the patient's artery within the sleeve to completely collapse. Thereafter, the cuff pressure is gradually reduced toward zero during which time the cuff continuously changes in pressure in an oscillating fashion due to the combination of (1) the internal blood pressure changes in the patient's artery and (2) changes in cuff pressure. The latter at any given time in the procedure is known and oscillatory changes in cuff pressure can be readily measured, for example with an oscilloscope. By using these two parameters in conjunction with information which may be made available from methods disclosed in the above-recited United States patents and the techniques of the present invention to be described hereinafter, it is possible to achieve the foregoing objectives in uncomplicated and reliable ways.

It should be noted at the outset that the typical 5" wide pressure cuff entirely surrounds a corresponding 5" length of artery. The tissue of the arm is for the most part incompressible, and therefore any change in the volume of the artery, caused for example by pulsations of blood, results in a corresponding change in the volume of air in the air bladder which is within the cuff and therefore adjacent to the arm. This change in air volume produces a small but accurately measurable pressure change in the air. This equivalence of pressure pulsations in the cuff bladder to volume pulsations of the artery is the essence of oscillometry.

BRIEF DESCRIPTION OF THE DRAWINGS

In order to more fully appreciate the various techniques of the present invention, the following more detailed information is provided in conjunction with the drawings where:

FIG. 1 (corresponding to FIG. 6 in U.S. Pat. No. 3,903,872) diagrammatically illustrates the shapes of successive cuff pressure versus time pulses (cuff pulses) as the measured cuff pressure changes from 90 Torr to 80 Torr to 70 Torr, assuming the patient has a diastolic pressure of 80 Torr.

FIG. 1A diagrammatically illustrates a full series of cuff pulses corresponding to those in FIG. 1 from a cuff pressure of 160 Torr to a cuff pressure of zero.

FIG. 2 diagrammatically illustrates what may be best referred to as a "transformation" curve or a volume/pressure (V/P) curve corresponding to the patient's arterial volume (V), that is, the volume of the patient's artery within the cuff (as measured by cuff volume) versus wall pressure ($P_w$) across the artery wall within the cuff and, superimposed on this curve, a curve which is intended to correspond to the actual blood pressure waveform of a patient, the two curves being provided together in order to illustrate the principles of oscillometry, as relied upon in the above-recited patents. As will be described below, arterial volume changes $\Delta V$ produce cuff pulses $P_c(ac)$ and so FIG. 2 also represents a curve which "transforms" blood pressure pulses into cuff pulses.

FIGS. 3 and 4 diagrammatically illustrate the transformation curve of FIG. 2 in ways which display techniques for obtaining a given patient's systolic and diastolic blood pressures in accordance with the Link and Link et al patents recited above.

FIG. 5 diagrammatically illustrates a curve corresponding to the compliance of the patient's artery, that is, a curve which displays the ratio $\Delta V/\Delta P_w$ against the arterial wall pressure $P_w$, where $\Delta V$ is the incremental change in the arterial volume corresponding to a preselected change in wall pressure $\Delta P_w$ for different cuff pressures, this latter curve being initially determined in order to provide the transformation curve (V/P curve) of FIG. 2 by means of integration, as will be seen. Because arterial volume changes produce cuff pulses, FIG. 5 also represents the relationship $\Delta P_c(ac)/\Delta P_w$.

FIG. 6 diagrammatically illustrates an actual blood pressure pulse for a given patient.

FIG. 7 diagrammatically illustrates a plotted waveform which approximates the actual blood pressure pulse of FIG. 6 and which is generated non-invasively in accordance with the present invention.

FIG. 8 diagrammatically illustrates a transformation curve similar to the one illustrated in FIGS. 2-4 but exaggerated along the vertical slope with enlarged portions of the diastolic decline forming part of an actual blood pressure waveform superimposed thereon.

FIG. 9 (a)-(d) diagrammatically illustrate four blood pressure waveforms having different blood pressure constants K.

FIG. 10 is a functional illustration of an arrangement for providing a curve which closely approximates a patient's actual blood pressure waveform and also provides the patients mean pressure and blood pressure constant.

FIG. 11 graphically displays the peak to peak amplitude A of various cuff pulses of FIG. 1A against cuff pressure.

FIG. 12 graphically illustrates a transformation curve corresponding to the one illustrated in FIG. 2 but generated from the information in FIGS. 1A and 11 only.

FIG. 13 illustrates the same curve as FIG. 21 normalized to zero volume at negative wall pressures and having superimposed thereon its differentiated curve.

FIG. 14 is a functional illustration of an arrangement for electronically generating the curves of FIG. 13.

FIGS. 15a, 15b, 15c and 15d graphically illustrate how a patient is subjected to cuff pressure with time in one down-ramp and three up-ramp modes (hereinafter referred to as down-ramp and up-ramp pressure cycles).

FIG. 16a graphically illustrates a series of down-ramp pressure cycles with time in which each cycle is carried out in accordance with the prior art.

FIG. 16b graphically illustrates a series of a down-ramp pressure cycles with time in which each cycle is carried out in accordance with the prior art.

FIG. 17 graphically illustrates a patient's transformation curve (corresponding to any of the transformation curves discussed previously) and a particular cuff pulse curve of the patient superimposed thereon.

FIG. 18 graphically illustrates a curve (corresponding to the curve of FIG. 5 in Link Pat. No. 3,903,872) for obtaining the diastolic pressure of the patient.

FIGS. 19a, 19b and 19c graphically illustrate three cuff pulses unique to the patient at respective cuff pressures of 50, 60 and 70 Torr.

FIG. 20 graphically illustrates the results of a stat mode of monitoring a particular patient's systolic, diastolic and mean pressures over an extended period of time in accordance with the present invention by taking successive measurements at closely spaced intervals but without having to subject the patient to cuff pressures above the systolic level each time.

FIG. 21A functionally illustrates an apparatus for monitoring a patient's systolic, diastolic and mean pressures over an extended period of time by taking successive measurements without having to subject the patient to cuff pressures as high as the patient's systolic pressure each time.

FIG. 21B illustrates a block diagram of an actual working embodiment of the apparatus of FIG. 21A (as well as the arrangements of FIGS. 10, 14 and 25).

FIG. 22 graphically illustrates two curves corresponding to the curve described in FIG. 5 of Link Pat. No. 3,903,872 at two different time intervals and over an applied cuff pressure range which includes a maximum cuff pressure which, at all times, is less than the patient's anticipated systolic pressure.

FIG. 23 graphically illustrates a patient's transformation curve which is the integration of the curve of FIG. 22 and which thereby corresponds to the patient's transformation curve over the cuff pressure range utilized to generate the curve of FIG. 23, and superimposed thereon is the patient's cuff pulse generated at a cuff pressure of 60 Torr.

FIG. 24 graphically illustrates the curve which is the integration of the curve of FIG. 22 and which thereby corresponds to the patient's transformation curve over the cuff pressure range utilized to generate the curve of FIG. 23, and superimposed thereon is the patient's cuff pressure generated at a cuff pressure of 60 Torr.

FIG. 25 functionally illustrates an apparatus for determining certain blood pressure parameters of a given patient including his systolic and diastolic pressures without having to subject the patient to cuff pressures as high as the patient's anticipated systolic pressure.

FIGS. 26–28A, B are flow diagrams corresponding to the techniques disclosed with respect to FIGS. 10, 14, 21A and 25.

DESCRIPTION OF THE PREFERRED EMBODIMENTS

Figure 28B:
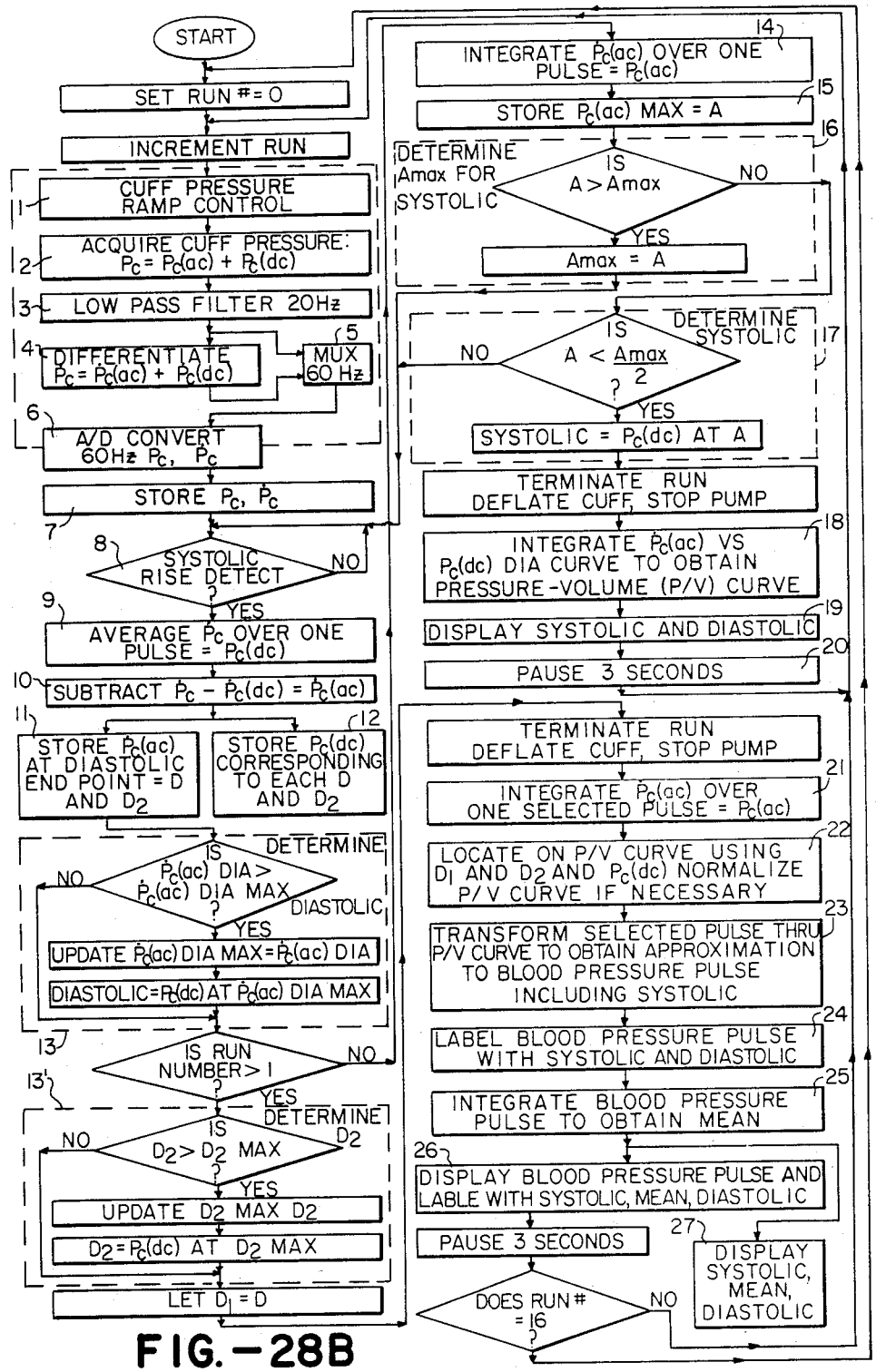

Turning first to FIG. 1, this figure diagrammatically illustrates three successive cuff pressure waveforms 10h, 10i and 10j which correspond to the change in arterial volume in a pressurized cuff, as described above, at three different cuff pressures, specifically cuff pressures of 90 Torr, 80 Torr and 70 Torr respectively. In actual practice, a greater number of cuff pressure waveforms (hereinafter referred to as cuff pulses) are generated starting at a high cuff pressure such as 160 Torr and ending at a cuff pressure of zero, as will be seen in FIG. 1A.

By generating these waveforms at known cuff pressures, both the diastolic and systolic pressures of a patient can be determined in accordance with the above-recited patents. While this will be explained in more detail below, it is important to note initially that each wave form has what may be referred to as a systolic rise $S_r$ at one end of the waveform, a diastolic decline $D_d$ at the opposite end and a maximum amplitude A. Moreover, for purposes of graphical illustration, because each applied cuff pressure to which the patient is subjected is a fixed value or at least a slowly changing value, it will sometimes be referred to hereinafter a $P_c(dc)$. At the same time, because the cuff pulses themselves are the result of a fluctuation in cuff pressure with time (due to the change in the patient's blood pressure), they will sometimes be referred to herein as $P_c(ac)$. Note also that $P_c(dc)$ may assume values from 0 to 250 Torr whereas the cuff pulses $P_c(ac)$ usually have peak to peak values less than 10 Torr.

The systolic rise $S_r$, the diastolic decline $D_d$ and the amplitude A vary from pulse to pulse for reasons to be explained hereinafter. It is because of these variations that the techniques disclosed in the Link and Link et al patents recited above can be used to determine the diastolic and systolic pressures. Specifically, as will be seen, when the diastolic pressure of a patient is equal to the applied cuff pressure $P_c(dc)$, the cuff pulse $P_c(ac)$ generated has a final diastolic decline which is greater in slope than the diastolic decline of any of the other cuff pulses. Thus, assuming that the final diastolic decline has a maximum slope at the cuff pulse 10i illustrated in FIG. 1, the patient providing these waveforms would have a diastolic pressure of 80 Torr. At the same time, this patient's systolic pressure can be determined by first finding which of the cuff pulses displays a maximum amplitude A and then, moving up in cuff pressure, finding the cuff pulse having half that amplitude. The cuff pressure responsible for producing this half amplitude pulse will approximately equal the patient's systolic blood pressure. In order to more fully understand these capabilities, reference is made to FIGS. 2–5 in conjunction with the above-recited Link and Link et al patents.

Turning now to FIG. 2, attention is directed to the curves illustrated there in order to explain why the cuff pulses of FIG. 1 result from changes in cuff pressure. The generally S-shaped transformation curve 12 illustrated is shown within a horizontal/vertical coordinate system where the horizontal axis is the transmural pressure or the wall pressure $P_w$ across the artery wall of a given patient, within the confines of the applied cuff. The vertical axis corresponds to the arterial volume V of the artery within the cuff, as measured by the internal volume of the cuff itself. In actuality, the transformation curve transforms applied blood pressure waveforms (which directly effect $P_w$ on the horizontal axis) to cuff pulses $P_c(ac)$ (which are dependent on arterial volume V within the cuff on the vertical axis). It will be appreciated that since the cuff pulses $P_c(ac)$ are caused by and are proportional to arterial volume changes $\Delta V$, the vertical axis of the S-shaped curve of FIG. 2 may be labelled by V or $P_c(ac)$ interchangeably depending on the phenomena being described. The proportionality of $P_c(ac)$ to V is valid over the central regions of the S-shaped curve of FIG. 2 but may be less valid for very small cuff pressures $P_c(dc)$. In order to fully understand this transformation curve (hereinafter also referred to as an arterial or a cuff curve), it is important to keep in mind the definition of $P_w$. The wall pressure $P_w$ of the artery of the patient at any given time is equal to the blood pressure $P_b$ of the patient within the artery at that time less the applied pressure of the cuff $P_c(dc)$. Thus:

$$P_w = P_b - P_c(dc) \quad (1)$$

For purposes of the present discussion, it will be assumed that pressure is measured in Torr (mmHg) and that the section of the horizontal axis to the right of the vertical axis represents positive wall pressures while the section of the axis to the left of the vertical axis represents negative wall pressures. As a result, when no pressure is applied to the cuff (e.g. $P_c=0$), $P_w$ at any given point in time is equal to the blood pressure of the patient at that time. As the cuff is pressurized, $P_w$ decreases (moves to the left along the horizontal axis). When the cuff pressure $P_c$ is equal to the blood pressure $P_b$ at any given point in time, $P_w$ at that moment is equal to zero (e.g. at the vertical axis). As the cuff pressure is increased beyond the blood pressure at any point in time, $P_w$ at that time becomes more negative (moves further to the left on the horizontal axis).

With the definitions of the vertical axis $P_c(ac)$ or V and the horizontal axis $P_w$ in mind, attention is now directed to an interpretation of the generally S-shaped cuff curve 12 within this coordinate system. For the moment, it is being assumed that this curve is characteristic of the particular patient being evaluated. That is, it is being assumed that the patient's artery within the cuff and therefore the cuff itself will change in volume along the S-shaped curve and only along the curve with changes in $P_w$. Hereinafter, with regard to FIG. 3, it will be shown that the transformation curve 12 of a given patient can be generated from his cuff pulses 10 and corresponding applied cuff pressures $P_c(dc)$. Thus, for the time being, it will be assumed that the transformation curve illustrated in FIG. 2 corresponds to that of the given patient.

With the foregoing in mind, the transformation curve of FIG. 2 will now be examined. Let it first be assumed that no pressure is applied to the patient's cuff so that $P_c(dc)$ equals zero. As a result, $P_w$ equals the blood pressure $P_b$ of the patient. In this regard, it is important to note that $P_b$ varies with time between the patient's diastolic blood pressure $P_b(D)$ and his systolic blood pressure $P_b(S)$. For purposes of this discussion, let it be assumed that these values are known and that specifically the patient's diastolic blood pressure is 80 Torr and his systolic blood pressure is 120 Torr. thus, with no pressure in the cuff, $P_w$ (the wall pressure or transmural pressure) oscillates back and forth with time between $P_b(D)$ and $P_b(S)$, that is, between 80 Torr and 120 Torr. This 40 Torr measuring band is illustrated by dotted lines in FIG. 2 at 14 and actually represents the patient's pulse pressure which is equal to 40 Torr in this case; pulse pressure=$P_b(S) - P_b(D) = 120 - 80 = 40$ Torr.

The patient's actual blood pressure waveform 15 is superimposed on the $V/P_w$ coordinate system in FIG. 2 within the pulse pressure band 14. As seen there, this waveform is made up of a series of actual blood pressure pulses 16 (pressure versus time), each of which corresponds to a single beat of the patient's heart. Note that each pulse starts at a minimum pressure (the diastolic pressure of the patient) at a given time $t_o$ and sharply increases along its leading edge which is the systolic rise $S_r$ until it reaches a maximum (the patient's systolic blood pressure), at which time it drops back down along a trailing edge which includes a dichrotic notch and a diastolic decline $D_d$ to the minimum pressure again at a second time $t_o$. At those points in time when the patient's blood pressure is at a minimum (that is, at the diastolic ends of pulses 16), the volume of the patient's artery and therefore the volume of the cuff is fixed by the arterial curve at the value indicated at $V_1(P_w=80)$. This corresponds to the minimum pressure level for the patient's cuff pulse $P_c(ac)$ at an applied cuff pressure $P_c(dc)$ of zero. On the other hand, whenever the patient's blood pressure is maximum (at the systolic end of each blood pressure pulse 16), the arterial curve fixes arterial and therefore cuff volume at the slightly higher value indicated at $V_w(P_w=120)$. This corresponds to the maximum pressure level for the patient's cuff pulse $P_c(ac)$ at an applied cuff pressure $P_c(dc)$ of zero. Therefore, it should be apparent that for each heart beat (e.g., the time increment from $t_o$ to $t_o$), assuming a cuff pressure $P_c(dc)$ of zero, the volume V (the cuff volume) moves between the values $V_1$ and $V_2$, thereby generating a cuff pulse 10q for each heart beat corresponding to those illustrated in FIG. 1 but at a cuff pressure $P_c(dc)=0$, as shown in FIG. 1A. Thus, as the patient's blood pressure rises from a minimum to a maximum, the volume of the artery rises from $V_1$ to $V_2$ in a generally corresponding manner (and so does the cuff pulse 10q) and as the patient's blood pressure drops back down to a minimum, the arterial volume falls from $V_2$ to $V_1$ in a generally corresponding manner (and so does the cuff pulse 10q). Thus, each of the cuff pulses 10 in FIG. 2 has a systolic rise $S_r$ and a diastolic decline $D_d$ corresponding to the systolic rise and diastolic decline of each blood pressure pulse 16.

Having shown how the cuff pulses 10q are dependent upon the transformation curve at an applied cuff pressure of zero, we will now describe how the transformation curve causes these cuff pulses to change with applied cuff pressure. Let us assume now an applied cuff pressure $P_c(dc)$ of 50 Torr. Under these conditions, $P_w$ oscillates back and forth between 30 Torr and 70 Torr. The 30 Torr value is determined by subtracting the cuff pressure $P_c(dc)$ of 50 Torr from the diastolic blood pressure $P_b(D)$ of 80 Torr and the 70 Torr value is determined by subtracting the same $P_c(dc)$ of 50 Torr from the systolic blood pressure $P_b(D)$ of 120 Torr. Thus, the entire 40 Torr band has merely been shifted to the left an amount equal to 50 Torr as indicated by the bank 14'. Under these circumstances, $P_w$ oscillates back and forth along a steeper segment of the arterial or transformation curve so as to cause the volume of the patient's artery and therefore the volume of the cuff to oscillate between the values $V_3$ and $V_4$. This results in the production of cuff pulses 10L at a $P_c(dc)$ of 50 Torr. Note that the amplitude of each cuff pulse 10L is greater than the amplitude of each cuff pulse 10q. This is because the 40 Torr band 14' at an applied cuff pressure of 50 Torr is on a steeper part of the volume curve than the band 14 at an applied cuff pressure of zero. Indeed, as we increase the cuff pressure $P_c(dc)$ (which decreases $P_w$) and therefore move the pressure band to the left on the horizontal axis, we first continue to move along steeper sections of the arterial curve and thereafter less steep sections. Therefore, the amplitude (see FIGS. 1 and 1A) of the corresponding cuff pulses 10q, 10L and so on will first increase to a maximum and then decrease again. At a cuff pressure $P_c(dc)$ of 100 Torr, the entire 40 Torr pressure band is shifted to the left so as to uniformly straddle opposite sides of the vertical zero axis, as indicated at 14''. This results in a corresponding cuff pulse 10g having approximately a maximum amplitude ($\Delta V_{max}$ in FIG. 2).

Moving still further to the left, at for example, an applied cuff pressure $P_c(dc)$ of 160 Torr, the entire 40 Torr band is moved a substantial distance to the left of the vertical axis, as indicated at 14''' such that the resultant change in volume (amplitude of the corresponding cuff pulse 10a) is quite small. By increasing the cuff pressure to even a greater amount, the band is moved still further to the left, eventually producing very small changes in volume V. From a physical standpoint, this represents a collapsed artery. In other words, sufficient cuff pressure $P_c(dc)$ is being applied over and above the internal blood pressure $P_b$ to cause the wall of the artery to collapse. At the other extreme, that is, when the cuff pressure $P_c(dc)$ is zero, there are no external constraints placed on the artery and the latter is free to fluctuate back and forth based on its internal pressure $P_b$ only. Between these extremes, the amplitude of cuff pulse 10 (e.g. $\Delta V$) will increase to a maximum and then decrease again, as stated. It is this latter characteristic which is used to determine the patient's systolic pressure in accordance with the previously recited Link et al patents, as will be described with regard to FIGS. 3 and 4. As previously mentioned, it should be noted that a blood pressure increase causes an arterial volume increase. This arterial volume increase causes a cuff bladder air volume decrease which in turn causes a cuff bladder air-pressure increase. Therefore, at a given applied cuff pressure $P_c(dc)$, a blood pressure increase results in a cuff air pressure increase. This is emphasized as follows:

| blood pressure increase | arterial volume increase | cuff air volume decrease | cuff air pressure increase |
|---|---|---|---|
| Thus: | | | |
| | blood pressure increase | cuff air pressure increase | |
| or | $\Delta P_b$ | $\Delta P_c$ (ac) | |

The converse to the above is also true, that is, a decrease in blood pressure results in a decrease in cuff air pressure. Therefore, at a given applied cuff pressure $P_c(dc)$, the amplitude $P_c(ac)$ or Pac of a Patient's cuff pulse varies directly with the patient's blood pressure pulse.

Referring to FIG. 3, the same transformation curve 12 illustrated in FIG. 2 is again shown but with a single superimposed pressure band 14'''' at a cuff pressure Pc of 120 Torr. Assume again that the diastolic pressure of the patient is 80 Torr and his systolic pressure is 120 which means that $P_c(dc)$ is equal to the patient's systolic pressure for band 14''''. Under these circumstances, $P_w$ oscillates back and forth within band 14'''' between wall pressures of −40 Torr and zero, as shown. This results in a change in arterial volume ΔV (e.g., the amplitude A of a corresponding cuff pulse) which is approximately equal to one-half of the maximum change in arterial volume (e.g., max cuff pulse amplitude). It may be recalled that a maximum change in volume ΔV max (and therefore a maximum cuff pulse amplitude) results from an applied cuff pressure $P_c(dc)$ of about 100 Torr (e.g. the pressure band 14'' in FIG. 2). Thus, when the cuff pressure Pc is equal to the patient's systolic blood pressure $P_b(S)$, the amplitude A of the resultant cuff pulse 10 is about one-half of the amplitude of the cuff pulse having a maximum amplitude. Therefore, a patient's systolic blood pressure can be determined by first generating a series of cuff pulses across the cuff pressure spectrum, as in FIG. 1A. From these pulses, the one having maximum amplitude Amax is determined and then the cuff pulse having half that amplitude (at a greater cuff pressure) is found. Once that pulse is found, its associated cuff pressure is assumed to be equal to the patient's systolic pressure. This is discuss more detail in Link et al U.S. Pat. Nos. 4,009,709 and 4,074,711 and means are provided i latter patents for electronically making these evaluations.

Returning to FIG. 2, it should be noted that the actual blood pressure waveform 15 is shown having a uniform repetition rate, for example 60 pulses/minute, and that each blood pressure pulse 16 making up this waveform is identical to the next one. Both of these aspects of the waveform are assumed for purposes herein. Moreover, each pulse has its own systolic rise $S_r$ and diastolic decline $D_d$, as mentioned heretofore. It should also be noted that the transformation curve 12 dictates the relationship between V or $P_c(ac)$ (on the vertical axis) and $P_w$ or $P_c(dc)$ (on the horizontal axis) at each and every point on the individual blood pressure pulse 16, not merely at the extreme diastolic and systolic end points of each pulse. At the same time it should be kept in mind that this means that the transformation curve dictates the relationship between the amplitude $P_c(ac)$ at any point on the blood pressure pulse 16 for any given applied cuff pressure $P_c(dc)$. Thus, one could measure the change in volume ΔV or the change between two different points in time along the diastolic decline of the blood pressure pulse for different cuff pressures $P_c(dc)$. In this case, the measuring band (e.g. the pressure difference between the two measuring points) is substantially narrower than band 14. As best illustrated in FIG. 4, $\Delta V_1'$ is determined for a cuff pressure $P_c(dc)$ of zero using the pressure band 18 which encompasses a small part of the diastolic decline of each blood pressure pulse 16. $\Delta V_2'$ is determined for a cuff pressure of $P_c(dc)$ of 50 Torr by shifting the band to 18' and, $\Delta V_3'$ is determined for a cuff pressure $P_c(dc)$ of 80 Torr (e.g. the patient's diastolic blood pressure) by shifting the band to 18''. Finally $\Delta V_4'$ is determined at an even higher cuff pressure by shifts to band 18'''. Note that ΔV' is maximum when the applied cuff pressure $P_c(dc)$ is equal to the patient's diastolic blood pressure. Therefore, by determining the relative change in volume ΔV' at the end of the diastolic slope of the patient's actual blood pressure waveform for each and every applied cuff pressure, the one cuff pressure producing a maximum volume change will correspond to the patient's diastolic blood pressure. The lowest pressure part of the diastolic decline $D_d$ forming part of each pulse 16 is particularly suitable for this purpose since it can be readily located during each cycle of the waveform. This is because it immediately precedes the systolic rise $S_r$ which is readily distinguishable each time it appears. This procedure is described in more detail in the previously recited Link Patent 3,903,872 along with means for carrying out this procedure electronically. Specifically, FIG. 5 in this patent illustrates the first time derivative of the measured cuff pressure pulse (hereinafter $\dot{P}$) at a time t within a patient's actual blood pressure pulse as a function of applied cuff pressure $P_c(dc)$. In the illustration just provided the first derivative corresponds to ΔV and the time t corresponds to the temporal center of bank 18, 18' and so on where t is on the diastolic decline of the blood pressure pulse close to the start of the next systolic rise. For purposes of convenience, the first time derivative of the measured cuff pressure and ΔV will be used herein interchangeably. However, it is to be understood that, in actuality, ΔV reflects actual changes in arterial volume whereas the first time derivative is a result of actual changes in cuff pressure (which correspond directly to ΔV).

This later point is further explained as follows. A straight forward variable to measure in the cuff pulse waveform is the slope of the pulse near the end of the diastolic decline; thus $\Delta P_c(AC)/\Delta t$ or $\dot{p}$ near the end of pulse or just prior to the next systolic blood pressure rise. This increment of time Δt is an easily fixed increment of time which corresponds to a change the blood pressure $\Delta P_b$ i.e., $\Delta P_b$=Constant × Δt where Δt and therefore $\Delta P_b$ are arbitrarily but conveniently chosen for best results. It follows that $\Delta P_c(ac)\Delta t$ constant × $\Delta P_c(ac)/\Delta P_b$, but the later differential relationship is the slope of the S-shaped curve of FIGS. 2, 3 and 4. We then have, $\dot{P}= \Delta P_c(ac)\Delta t$ constant × $P_c(ac)/\Delta P_b$=constant ×constant × $\Delta V/\Delta P_b$ or $\dot{P} \sim \Delta V/\Delta P_b$, and finally $\dot{P} \sim \Delta V$ for a constant $\Delta P_b$. In all of this, $\Delta P_b = \Delta P_w$ by the definition $P_w = P_b - P_c(dc)$ where $P_c(dc)$ is constant or slowly changing.

The foregoing discussions for obtaining a given patient's systolic and diastolic blood pressures have assumed that the patient's transformation curve was known and corresponded to the one illustrated in FIGS. 2, 3 and 4. It is however possible to determine the patient's own transformation curve, if not already known, using the principles associated with FIG. 4. Specifically, using the narrower bands 18, 18' and so on as measuring bands, the change in volume ΔV (e.g., the change in cuff volume) or P resulting from different applied cuff pressures $P_c(dc)$ is plotted, as shown in FIG. 5. Thus at an applied cuff pressure $P_c(dc)$ of zero, there is a relatively small change in volume ΔV or a small $\dot{P}$, as evidenced by the small $\Delta V_1'$ in FIG. 4. As the cuff pressure $P_c(dc)$ increases, the change in volume ΔV or $\dot{P}$ continues to increase to a maximum ($\Delta V_3'$ in FIG. 4) and then decreases. In mathematical terms, this curve represents incremental changes in volume divided by incremental changes in pressure of $\Delta V/\Delta P$ (FIG. 5) or actually changes in $\dot{P}$ as $P_w = P_b - P_c(dc)$ changes. By integrating this $\dot{P}$ versus $P_w$ curve we obtain the transformation curve or the $V/P_w$ curve of FIGS. 2-4.

Having discussed FIGS. 1-5 in regards to the prior art techniques for obtaining diastolic and systolic blood pressures and for generating a $\dot{P}$ versus $P_w$ curve and a transformation curve for a given patient in accordance with the techniques described above and in the above-recited Link and Link et al patents, attention is now directed to the various aspects of the present invention in conjunction with FIGS. 6–9. Turning first to FIGS. 6–8, attention is now directed to a technique provided in accordance with the present invention for generating a waveform which closely approximates an individual patient's actual blood pressure waveform (for example, the blood pressure pulse 16 in FIG. 2) without using an invasive device. For purposes of illustration, the assumed actual blood pressure pulse is shown graphically in FIG. 6 at 20 where the patient's blood pressure (the vertical axis) is measured against time (the horizontal axis). From previous discussions and a knowledge of the subject matter of Link Pat. No. 3,903,872 and Link et al. Pat. Nos. 4,009,709 and 4,074,711, the individual patient's diastolic and systolic pressures $P_b(D)$ and $P_b(S)$ can be first determined, thereby providing the minimum and maximum vertical points on the pulse as seen in FIG. 6. At the same time, since the systolic rise (leading edge) of the actual pulse is readily detectable, the pulse's beginning and end points time wise ($t_o$ and $T_o'$) are also readily detectable. Therefore, using the same coordinate system in FIG. 7 we will now describe a method for non-invasively determining the important features of the blood pressure pulse shown in FIG. 6 and thus providing a useful approximation of the whole pulse. As appears in FIG. 6, the horizontal (time) axis can be made to represent the patient's diastolic blood pressure with $T_o$ being provided at the vertical axis, indicating the beginning of the waveform and $t_o'$ a second point indicating the end of that waveform and the beginning of the next one. A horizontal line $L_1$ can then be drawn above the time axis at the patient's systolic blood pressure. A single point on this horizontal line can then be established as $t_o''$ in the frame of reference just established.

Having graphically provided the time and pressure axes t and P, the points $t_o$ and $T_o'$ and the dotted horizontal line $L_1$ at the patient's systolic blood pressure, and the point $t_o''$ on the horizontal line, attention is now directed to the way in which the waveform is completed in a non-invasive manner. To this end, reference is directed to FIG. 8 which is similar to FIG. 4, with one exception. It may be recalled from the previous discussion of FIG. 4 in conjunction with Link Pat. No. 3,903,872, a patient's diastolic blood pressure can be determined electronically by varying the applied cuff pressure $P_c(dc)$ and detecting the resultant change in cuff volume $\Delta V$ or $\dot{P}$ (the first time derivative of the measured cuff pressure pulses) within the same pressure or measuring band (e.g., the band 18, 18' and so on in FIG. 4) in the patient's actual blood pressure waveform, that is, along the diastolic decline just before the systolic rise. The cuff pressure $P_c(dc)$ resulting in a maximum change in arterial volume $\Delta V$max or in a maximum $\dot{P}$ corresponds to the patient's diastolic blood pressure. The physical components for carrying out this process are described in the '872 patent and reference is made thereto. These components include means serving as a generator for detecting the beginning of the patient's systolic rise and measuring back therefrom, for example 50 milliseconds, in order to provide repeatedly a 50 millisecond measuring band. During that time the change in cuff volume $\Delta V$ or $\dot{P}$ is measured by cooperating means for each applied cuff pressure $P_c(dc)$. Means are also provided for determining when $\Delta V$ or $\dot{P}$ is at a maximum and for reading out the cuff pressure $P_c(dc)$ at $\Delta V$max or $\dot{P}$ max, this latter cuff pressure corresponding to the patient's diastolic pressure.

In accordance with the present invention and as described generally in the '872 patent, the generator just recited can be used to provide a series of identical measuring bands of width $\Delta t$ moving back in time from the systolic rise at $t_o'$, specifically from $t_1 - 2/\Delta t$ to $t_1 + 2/\Delta t$;

from $t_2 - 2/\Delta t + 2/\Delta t$;

and generally from $t_n - 2/\Delta t$ to $t_n + /\Delta t$ as shown in FIG. 8, rather than a single band as in FIG. 4. These bands are indicated at $22_1$, $22_2$, $22_n$ and so on. The generator means forming part of the components described in the '872 patent can be readily used or easily modified to provide these different points in time and therefore the different bands $22_1$, $22_2$, $22_n$ and so on. During each measuring band the cuff pressure $P_c(dc)$ is varied in order to find the cuff pressure which results in a maximum change in cuff volume $\Delta V$max or maximum $\dot{P}$. That cuff pressure corresponds to the patient's actual blood pressure at the point in time in the actual blood pressure curve. Thus, for example, if during the measuring band $22_1$ $$\left(t_1 - \frac{\Delta t}{2} \text{ to } t_1 + \frac{\Delta t}{2}\right),$$

$P_c(dc)$ is found to equal $P_b1$ at a $\dot{P}$ max than the patient's actual blood pressure at the time $t_1$ (where $t_1$ is temporally the center point of band $22_1$) is equal to $P_b1$. This can be repeated (preferably all in one run) for the measuring bands $22_2$ and $22_n$ and so on for providing pressure points $P_b2$ to $P_bn$ corresponding to times $t_2$ to $t_n$ in the graph of FIG. 7 where $t_2$ to $t_n$ are temporally the center points of their respective bands. While FIG. 8 shows only two such bands along the diastolic decline, they can extend entirely back to the beginning of the pulse (time $t_o$), except along any segments of the pulse where the slope is zero, as for example at the systolic pressure point or at the peak of the dichrotic notch, as will be pointed out below. All of the intermediate points (except at zero slopes) between $t_o$ and $t'_o$ can be found in this way.

Only if the measuring bands $22_1$, $22_2$ and so on are selected to fall on parts of the waveform of FIG. 6 which have finite positive or negative slope, will this procedure be accurate. If by example the measuring band were located at time $t_4$ at a position of zero slope on the waveform of FIG. 6, the resulting slope of the cuff pressure pulse at the time $t_4$ would also be zero for all values of the cuff pressure. In this latter case the sensitivity of the method becomes zero when the slope of the true waveform becomes zero. With the exception of all these zero slope points on the waveform; any other position on the waveform at general time $T_n$ can be located by observing the general applied cuff pressure $P_c$ at which the slope of the cuff pressure pulse has a maximum at time $T_n$. The observed cuff pressure $P_c(n)$ may then be plotted against $t_n$ as a valid point on the waveform. This is made clear in FIG. 7 in which the areas of the waveform which are unmeasurable or poorly measurable by this method are indicated by dotted lines. It is also described generally in Link U.S. Pat. No. 3,903,872, although not in detail.

The foregoing has been a discussion of how a particular patient's actual blood pressure waveform can be closely approximated without an invasive device. This may be an important diagnostic tool to a doctor, especially if it turns out that his patient has an irregular waveform. This is best exemplified in FIGS. 9a-d which diagrammatically illustrate a number of waveforms having different mean values. The mean pressure $P_b(M)$ of a blood pressure waveform is equal to the diastolic blood pressure $P_b(D)$ plus a particular fraction K of the difference between the patient's systolic blood pressure $P_b(S)$ and his diastolic blood pressure. Equation 2A shows this and equation 2B shows the same thing in a convenient short hand notation.

$$P_b(M) = P_b(D) + K(P_b(S) - P_b(D)) \quad (2A)$$

$$M = D + K(S - D) \quad (2B)$$

Noting that the mean pressure M can be calculated by integrating the waveform (its pressure amplitude P) over time T (the duration of the waveform) so that:

$$M = \frac{\int_0^T P\,dt}{T} \quad (3)$$

and:

$$K = \frac{M - D}{S - D} = \frac{\frac{\int_0^T P\,dt}{T} - D}{S - D} \quad (4)$$

With the above equations in mind, the FIG. 9a waveform can be shown to have a K value (which is commonly referred to as the blood pressure constant) of about 0.50. The FIG. 9b waveform approximates a K value of 0.6 while the FIG. 9c waveform approximates a K value of 0.2. Finally, the FIG. 9d waveform approximates a K value of 0.33. This latter waveform most closely corresponds to a healthy blood pressure waveform and therefore some diagnostic devices of the prior art purport to calculate mean blood pressures by assuming a K value of 0.33. With this assumption of K=0.33 along with the patient's diastolic and systolic blood pressures, a calculation of the mean pressure using equations 2A and B can be done. Of course, this can be quite dangerous if the particular patient actually has a blood pressure constant of, for example, 0.60 or 0.20. However, by generating the approximated waveform illustrated in FIG. 7, all guess work regarding the patient's mean blood pressure and blood pressure constant K is eliminated. In fact, once the approximated waveform is determined, it can be integrated electronically so as to calculate the mean pressure $P_b(M)$ which might be helpful to the doctor and from this the blood pressure constant K can be readily calculated. Suitable means can readily be provided to make these various calculations.

As a result of the various aspects of the present invention thus far described, a diagnostic tool can be provided which not only provides a patient's diastolic and systolic blood pressures non-invasively but also provides a close approximation of the patient's actual blood pressure waveform as well as his mean pressure and blood pressure constant, again non-invasively. This tool or arrangement is shown in FIG. 10 including suitable cuff means generally indicated at 30 in position around the arm of a patient in the normal operating manner and maintained at different pressure levels from zero pressure to, for example, 160 Torr by suitable means 32. The resultant cuff pulses are monitored by transducer 34. Suitable and readily providable electronic means 35 serve to receive these pulses and from this information can provide the patient's diastolic and systolic blood pressures along with his transformation curve in accordance with the Link and Link et al patents. Means 35 also includes readily providable circuitry for providing the intermediate pressure points at times $t_1$, $t_2$, $t_3$, and so on shown in FIGS. 6–8 and with this information further readily providable circuitry for graphing the waveform in FIG. 7 on an oscilloscope or monitor 36. In addition means 35 can also include circuitry for calculating the mean pressure $P_b(M)$ and blood pressure constant K from this waveform and equations 2–4 above. An actual working embodiment of this overall arrangement is shown by block diagram in FIG. 21B which will be discussed hereafter.

Having discussed FIGS. 1–5 in regards to the prior art techniques for obtaining diastolic and systolic blood pressures for a given patient in accordance with the techniques described in the above-recited Link and Link et al patents and FIGS. 6–10 regarding techniques for generating a patient's own blood pressure curve and its mean value, attention is now directed to another aspect of the present invention, in conjunction with FIGS. 11–14. Turning now to FIGS. 11–14 in conjunction with FIG. 1A, attention is directed to a technique for generating a transformation curve for a given individual in accordance with the present invention. As stated previously, FIG. 1A illustrates a particular patient's cuff pulses 10a, 10b and so on, as read out on an oscilloscope, for varying applied cuff pressures $P_c(dc)$ starting with a cuff pressure of 160 Torr (pulse 10a) and ending with a cuff pressure of zero (pulse 10q). Note that the peak to peak amplitude (A) of each cuff pulse has been measured and so indicated in FIG. 1A. As will be seen below, by using only this information and the patient's diastolic and systolic pressures which may be determined in any suitable manner, for example in accordance with the previously recited Link and Link et al patents, the particular patient's own transformation curve and its derivative (corresponding to his arterial compliance ($dV/dP_w$) curve) can be generated in a way which is different than has been done heretofore.

Referring to FIG. 11, the peak to peak amplitude values (A) measured from FIG. 1A have been graphically plotted against applied cuff pressure and a resultant curve 40 drawn. Using information taken from this curve and the patient's diastolic and systolic blood pressures, the S-shaped transformation curve 42 of FIG. 8 may be plotted. In order to more fully understand how this is accomplished, it must be kept in mind that the patient's diastolic and systolic pressures together provide a pulse pressure band (e.g. a measuring band) corresponding to the band 14 illustrated in FIG. 2. Assuming the patient's diastolic blood pressure is 80 Torr and his systolic blood pressure is 120 Torr, this band is precisely 40 Torr wide. It must also be kept in mind that the transformation curve 42 is plotted in an x-y coordinate system in which the x-axis (the transmural axis) corresponds to $P_2$ (the wall pressure of the patient's artery) and the y-axis corresponds to relative arterial volume or $P_c(ac)$, as previously described with respect to FIG. 2. As a reminder, $P_{wall} = P_{blood} - P_{cuff}$ or $P_w = P_b - P_c(dc)$. Thus, with a cuff pressure $P_c(dc)$ of zero, the measuring band is between 80 Torr and 120 Torr and the peak to peak amplitude of the cuff pulse is 0.1 Torr which corresponds (is in direct proportion) to the change in arterial volume ($\Delta V$) resulting from this cuff pressure. In other words, as the patient's blood pressure rises and falls within the measuring band of 80 Torr and 120 Torr, V changes in amount so as to produce a cuff pulse amplitude A of 0.1Torr. This point can be plotted in FIG. 12 as point 1 on the transformation curve which transforms variations in blood pressure $P_b$ or wall pressure $P_w$ into cuff pulses $P_c(ac)$.

At an applied cuff pressure of 40 Torr, the wall pressure $P_w$ oscillates back and forth within the 40 Torr measuring band between 80 Torr and 40 Torr. As seen in FIGS. 1A, 11 and 12, this results in a peak to peak amplitude of 0.50 Torr and a directly proportionate change in $\Delta V$. This may be plotted as point 2. Additional points 3, 4 and 5 have been plotted in FIG. 12 corresponding to cuff pressures of 80, 120 and 160. While only five points were plotted, it should be understood that points corresponding to all of the cuff pressures actually measured in FIG. 1A and even those interpolated from the curve of FIG. 11 could have been plotted. From these points, the transformation curve 42 illustrated in FIG. 12 can be readily drawn. This curve is reproduced in FIG. 13 with the axis corresponding to $P_w$ moved downward, as shown. Once the transformation curve is generated, the patient's differential relationship $\Delta P_c(ac)/\Delta P_w$ or equivalently his compliance curve $dV/dP_w$ 43 can be generated by differentiating the transformation curve.

It is noted that the oscillometric cuff pulse amplitudes A shown in FIG. 1a often do not become zero for even very large values of the cuff pressure but approach a small and fairly constant value for large cuff pressure. This small value may be subtracted from each of the other amplitude values A in the table of FIG. 1a and graphed in FIG. 11. The resulting slightly reduced values A could then be utilized to provide a somewhat improved $P_c(ac)/P_w$ or $V/P_w$ curve by using the method described above.

FIG. 14 illustrates means 44 for receiving the various cuff pulses corresponding to those in FIG. 1A from a given individual through a cuff (45) applied to the individual's arm and a transducer 34 forming part of means 44. Means 44 then extracts the peak to peak information and upon receiving the patient's diastolic and systolic blood pressures from suitable inputs shown in FIG. 14 is able to act on this information so as to generate the transformation $P_c(ac)$ vs $P_w$ and its derivative $\Delta P_c(ac)/\Delta P_w$ curves 42 and 43, respectively, which can be permanently recorded or placed on an oscilloscope, as generally indicated at 46. The electronics necessary to make means 44 function in this manner can be readily provided in view of the teachings herein. The block diagram of FIG. 21B (to be discussed hereinafter) serves as an actual working embodiment of this arrangement of FIG. 14.

The foregoing descriptions may be separated into three categories. The description associated with FIGS. 1-5 corresponds to prior art techniques for obtaining diastolic and systolic blood pressures for a given patient in accordance with the techniques described in the above-recited Link and Link et al patents. The description associated with FIGS. 6-10 is directed to techniques for generating a patient's own blood pressure curve and its mean value as described and claimed in applicant's parent application Ser. No. 622,213 filed June 19, 1984 and as generally alluded to in Link Pat. No. 3,903,872. Finally, the description associated with FIGS. 11-14 is directed to techniques for generating the patient's own transformation curve as disclosed and claimed in applicant's own parent application Ser. No. 622,080 filed June 19, 1984. Having provided these descriptions, attention is now directed to still further aspects of the present invention in conjunction with FIGS. 15-25.

Referring first to FIGS. 15-21, these Figures correspond to what may be referred to as a rapid or stat mode for monitoring a patient's systolic, diastolic and mean pressures over an extended period of time by taking successive measurements at closely spaced intervals throughout the period. Moreover, while this monitoring technique requires that the patient be subjected to elevated cuff pressures over this period, the present invention minimizes the discomfort resulting from being subjected to these pressures. In order to more fully appreciate this, attention is first directed to FIG. 15a which graphically illustrates how a patient is subjected to cuff pressure during one full down-ramp cycle. More specifically, as seen in FIG. 15a, the horizontal axis represents time while the vertical axis represents the cuff pressure to which the patient is subjected during the full cycle (which is shown to be 20 seconds long). The curve (or full cycle as it will be called) is indicated at 50a and shows that the patient is subjected to an initial pressure pump up and then to a down-ramping pressure starting with a cuff pressure of 170 Torr and ending at a cuff pressure of zero. FIGS. 15b, c and d illustrate up-ramp cycles to be discussed hereinafter.

For purposes herein, it is assumed that curves 50a, 50b, 50c and 50d are linear and can be made so in accordance with devices such as described in applicant's copending patent application Ser. No. 670,213, filed Nov. 13, 1984 entitled LINEAR PRESSURIZING AND DEPRESSURIZING DEVICE AND ITS METHOD OF USE, now U.S. Pat. No. 4,587,974. However, it is to be understood that the ramps could also be non-linear as is typical in the prior art. In either case, in accordance with the techniques previously described herein and in the previously recited Link and Link et al patents, it was necessary to subject a given patient to cuff pressures within a range which included the patient's anticipated diastolic and systolic pressures in order to determine these latter pressures and the patient's mean pressure. Thus, if it is assumed that a given patient's diastolic pressure is 80 Torr and his systolic pressure is 140 Torr, heretofore it was necessary to subject the patient to a cuff pressure greater than 140 Torr, for example the 170 Torr level shown in FIG. 15a. Thus, it was typical to provide the full cycle ramp shown in this latter figure. FIG. 15b illustrates a full cycle also, but in an up-ramp mode.

The graphic illustration in FIG. 15a not only depicts a typical prior art full-cycle down-ramp but also can be shown to represent the level of comfort to the patient by taking the areas under the curves. By way of explanation it is reasonable to estimate a patient's discomfort from taking a blood pressure measurement as the product of the cuff pressure and the time of pressurization. Further, by experience, we can assign the time during which the cuff pressure is less than diastolic as mildly discomforting, and during which the cuff pressure is greater than diastolic pressure as greatly discomforting (the artery is being completely collapsed in this high pressure region). These two levels of discomfort are shown in FIGS. 15a, 15b, 15c, 15d, 16a and 16b. We define the sum of the two discomfort levels as the discomfort coefficient and these are also included in the figures. Thus, the total area under curve 50a is equal to 1960 Torr-seconds. This may be referred to as the patient's "discomfort coefficient". Obviously, the greater this coefficient the less comfortable the patient is. This is especially true if it is necessary to monitor the patient over an extended period of time and thereby subject him to a number of pressure cycles, as illustrated, for example, in FIG. 16a. As shown there, the patient's diastolic, systolic and mean pressures (also referred to herein as critical pressures) are monitored over a period of 100 seconds requiring five full cycles of the type illustrated in FIG. 15a. Therefore, over this entire extended period, the patient's total discomfort coefficient is equal to 9800 Torr-seconds (5 cycles at 1960 Torr-seconds/cycle). This is typical for existing "down-ramp" machines.

As will be seen below, by the technique disclosed herein it is possible to reduce substantially the above described discomfort coefficient over an extended monitoring period while monitoring the same critical pressures throughout this period. This is best illustrated in FIG. 16b in conjunction with FIGS. 15b and 15d. As shown in FIG. 16b, the patient is subjected initially to a full up-ramp cycle 50b but is then subjected to reduce up-ramp "stat" cycles 50d shown in FIG. 15d. Returning to FIG. 15d, the reduced stat cycles 50d is shown and is only 12 seconds long and has a maximum pressure of 90 Torr. therefore, its discomfort coefficient 540 Torr-seconds as opposed to the 1500 Torr-second discomfort coefficient of the full cycle 50b. As will be seen hereinafter, once the patient's diastolic and systolic pressures are established as a result of the initial full cycle 50b, it is possible in accordance with the present technique to obtain not only the patient's diastolic pressure but also his systolic pressure and mean pressure as a result of measurements utilizing the smaller stat cycles. It is only necessary that the patient be subjected to a cuff pressure slightly greater than his anticipated diastolic pressure during each of these successive measurements.

Thus, as illustrated in FIG. 16b, five measurements are in fact made over the same 100 second period illustrated in FIG. 16a. However, the total discomfort coefficient is 3740 Torr-seconds rather than 9800 Torr-seconds as in the case of FIG. 16a. While the stat cycles are illustrated in FIG. 16b at spaced intervals in time over the 100 seconds it is certainly possible to obtain a greater number of measurements over the same period or obtain the same number of measurements over a lesser period by generating the stat cycles immediately after one another and after the full cycle 50b. Also, while both the full and stat cycles have been generated as up-ramps, it is to be understood that they could just as easily be generated as down-ramps. In fact, if it is desired, the full cycle mode can be initially provided in duplicate as a back to back up-ramp and down-ramp. In this way, the full cycle or "parameter determining" cycle as it may be referred to can be duplicated in order to obtain two direct measurements for the patient's critical pressures initially.

The foregoing discussion of FIGS. 15a, b, d, 16a and 16b has assumed that it is possibe to determine a patient's systolic pressure without having to subject the patient to a cuff pressure at that level, once the patient's systolic pressure is initially measured during a parameter determining cycle. Attention is now directed to FIGS. 17, 18 and 19a, b, and c in order to understand how this is accomplished.

Referring first to FIG. 17, the particular patient's transformation curve 54 is illustrated. This curve was previously described herein and, as described, it can be readily generated by subjecting the patient to the full range of cuff pressures corresponding to up-ramp 50b and determining the patient's diastolic and systolic pressures during this up-ramp cycle. Therefore, during the monitoring procedure illustrated in FIG. 16b, the patient's particular transformation curve 54 can be generated during the initial full cycle 50b along with the patient's diastolic, systolic and mean pressures. In the following stat cycle (and all of the subsequent stat cycles) it is not possible to obtain the patient's systolic pressure in the same manner since he is not subjected to a cuff pressure at least as great as his systolic pressure. Nevertheless, it is possible to obtain the patient's systolic pressure at that time by using the transformation curve generated during the first cycle, as will be seen.

The diastolic pressure is obtained in the manner described in Link Pat. No. 3,903,872 utilizing the curve illustrated in FIG. 18. As stated previously, this curve corresponds to the curve in FIG. 5 of this latter patent for cuff pressures within the stat cycle, that is up to a maximum of 100 Torr. Thus, the horizontal axis represents applied cuff pressures $P_c(dc)$ up to 100 Torr and the vertical axis represents the first derivative ($\dot{P}$) of the measured cuff pressure pulses at a specific time in the patient's actual blood pressure pulse or cycle. By generating this curve at the appropriate time in the patient's blood pressure cycle (near the diastolic end point) the patient's diastolic pressure is readily determined. Specifically, as previously described herein and as described in the '872 patent, the applied cuff pressure $P_c(dc)$ responsible for generating $\dot{P}$ max on the curve in FIG. 18 (corresponding the maximum change in arterial volume at the diastolic end point) is equal to the patient's diastolic pressure. Thus, in the curve of FIG. 18, it is seen that the patient's diastolic pressure is 80 Torr.

During a stat cycle, each time the patients heart beats, a cuff pulse $P_c(ac)$ is generated corresponding to the then applied cuff pressure $P_c(dc)$. These pulses, three of which are illustrated in FIGS. 19a, 19b and 19c, are used to generate the curve of FIG. 18 to determine the patient's diastolic pressure. At least one of these cuff pulses is used in conjunction with the patient's transformation curve 54 illustrated in FIG. 17 and the patient's diastolic pressure of 80 Torr produced as a result of the curve in FIG. 18 to determine the patient's systolic pressure during that cycle. Returning to FIG. 17, attention is directed to the way in which this is accomplished. Specifically, let it be assumed that the cuff pulse 56a generated at a cuff pressure of 50 Torr, as illustrated in FIG. 19a, is used in conjunction with the transformation curve and the patient's diastolic pressure.

At the outset, it is necessary to locate the base of the cuff pulse 56a (its diastolic level) on the vertical axis of the transformation curve 54. To this end, the transmural pressure on the horizontal axis ($P_w$) corresponding to the patient's diastolic pressure at a cuff pressure of 50 Torr is located. This point is the diastolic blood pressure of the patient minus the cuff pressure or 80 Torr minus 50 torr which is 30 Torr. This 30 Torr point is located as illustrated in FIG. 17 and a vertical line 57 (actually a series of arrows) is drawn up to the point at which it intersects the transformation curve. That point determines the horizontal base of the cuff pulse 56a of FIG. 19a, as indicated by horizontal line 58. The cuff pulse is set on line 58 as shown. Thereafter, a horizontal line 60 is generated from the systolic level of the cuff pulse to the transformation curve. At the point of intersection of this latter curve with line 60, a further vertical line 62 is drawn downward to its point of intersection with the transmural pressure axis. As illustrated, this point of intersection is at 90 Torr. This 90 Torr value corresponds to $P_w$ as described previously at a cuff pressure $P_c(dc)$ of 50 Torr. Thus, the patient's actual blood pressure at this point (which corresponds to his systolic pressure) is the 90 Torr value plus the cuff pressure of 50 Torr or 140 Torr ($P_w + P_c(dc) = P_b$).

In view of the foregoing, it should be apparent that the systolic pressure of a patient can be obtained during a stat cycle, that is, without subjecting the patient to pressures as high as his systolic pressure so long as a prior parameter determining full cycle is carried out to determine the patient's systolic pressure directly at least once in order to generate the transformation curve 54. For purposes of accuracy it may be desirable to carry out the procedure described immediately above for obtaining the patient's systolic pressure using additional cuff pulses at other pressures, for example cuff pulses 56b and 56c in addition to the cuff pulse 56a. If the systolic pressures obtained from these different measurements are different, they can be averaged to provide an average systolic pressure. At the same time, once the patient's diastolic and systolic pressures are determined as a result of the stat cycle, techniques previously described herein can be utilized to obtain the patient's mean pressure during that same stat cycle i.e., the entire cuff pulse curve 56a can be transformed through the transformation curve 54 and the mean blood pressure curve obtained by integration.

FIG. 20 graphically illustrates the results of the monitoring procedure just described. The horizontal axis represents time and the vertical axis represents the patient's diastolic, mean and systolic pressures at different times corresponding to the different measurements. The first measurement corresponds to a full cycle mode while the subsequent ones may correspond to stat modes or it maybe desirable to provide a full cycle mode periodically in order to reconfirm or modify the patient's transformation curve 54. In either case, the patient is subjected to a lower discomfort coefficient than would be the case if each measurement required a full operating cycle.

Referring now to FIG. 21A, this Figure functionally illustrates an apparatus 64 for carrying out the procedure just described. This apparatus includes a suitable blood pressure cuff 66 positioned at the appropriate location adjacent an artery of a patient. Means generally indicated at 68 are provided for pressurizing the cuff to different levels sufficient to provide the full cycle 50b and the stat cycle 50d. The resultant cuff pulses including those illustrated in FIGS. 19a, b, and c and are produced by suitable circuitry 70 capable of holding the cuff pulses including, for example, those illustrated in FIGS. 19a, b and c, in memory. Circuitry generally indicated at 72 is responsive to the cuff pulses produced during the initial parameter determining cycle for determining the patient's diastolic and systolic pressures during that cycle. These values and the cuff pulses produced by circuitry 70 are input to circuitry 74 for generating the patient's transformation curve which is stored in memory therein. At the same time, circuitry 74 includes suitable means for determining the patient's mean pressure during the parameter determining cycle.

During each of the subsequent stat cycles, means 68 pressurizes cuff 66 to provide the stat cycle 50d and circuitry 70 produces the corresponding cuff pulses. Circuitry 72 is responsive to these cuff pulses for determining the patient's diastolic pressure only since the cuff 66 is not pressurized to a sufficiently high level to determine the patient's systolic pressure. The diastolic pressure determined during this stat cycle is input to circuitry 76 along with the cuff pulses from circuitry 70 for at least one or a group of the cuff pulses such as those illustrated in FIGS. 19a, b and c and the patient's transformation curve is held in the memory of circuitry 74. Circuitry 76 acts on this information to determine the patient's systolic blood pressure by carrying out the procedure described with regard to FIG. 17. This pressure value may be fed back into circuitry 74 so that the latter can also provide the patient's mean pressure during this latter cycle.

As indicated above, FIG. 21a is a functional illustration of an apparatus 64 for carrying out the techniques associated with FIGS. 15-20. FIG. 21b is a block diagram of an actual working embodiment of this apparatus, which in FIG. 21b is indicated at 64'. The apparatus shown there (in block diagram) includes a blood pressure cuff or pressure pad 66' positioned at an appropriate location around (in the case of a cuff) or adjacent (in the case of a pad) a suitable artery of a patient. In this latter regard, it is to be understood that either a cuff or a pad may be utilized. For purposes herein, where reference is made to a cuff only, it is to be understood that a pad could be readily substituted therefore, although a different artery may have to be selected.

A pump and suitable pneumatic controls generally indicated at 68' are provided for pressurizing the cuff (or pad) to different pressure levels sufficient to provide the full-up-ramp cycle 50b and the stat cycle 50d illustrated in FIGS. 15b and d, respectively, or any other type of cycle such as the cycle 50a and 50c illustrated in FIGS. 15a and c, respectively. A pressure transducer illustrated at 69' couples the cuff or pressure pad to a combination of amplifiers and band pass filters generally indicated at 70' for producing cuff pulses such as the ones illustrated in FIGS. 19a, b, and c.

An analog MUX, an A/D converter and a 16-bit microcomputer (or any other suitable computer means) indicated generally at 71', 72' and 73', respectively, interconnected in the manner illustrated in FIG. 21b, cooperate to provide means for digitizing the analog cuff pressures, i.e., $P_c(ac)$ and $P_c(dc)$. The microcomputer or computer generally is controlled by a suitable program stored in ROM 74' in order to carry out the necessary steps of the overall apparatus 64'. This program may vary in length from for example 1K bytes to as much as 32k bytes, depending on accuracy and other factors. The digitized value of cuff pressure $P_c(ac)$ and $P_c(dc)$ and other necessary information, e.g., the transformation curve generated during each initial parameter determining cycle, are stored by the computer 73' in a RAM 75'. The computer having calculated the various blood pressures, outputs the results to a monitor 76', printer 77', LED display 78' or perhaps to another computer 79'. It can be seen that the RAM memory 75' must be sufficiently large to store the various cuff pulses as well as the transformation curves described above.

The block diagram illustrated in FIG. 21b has been described specifically with respect to apparatus 64', that is, as an apparatus for carrying out the technique associated with FIGS. 15-21a. However, it is to be understood that this same arrangement illustrated in FIG. 21b may serve as an actual working embodiment for carrying out the functional steps associated with the arrangements of FIGS. 10 and 14. In the case of the arrangement of FIG. 10, the ROM 74' would contain a suitable program for operating the microcomputer or computer 73' so as to act on the digitized cuff pressures in a way which produces the necessary information to generate and output the curve of FIG. 7. In the case of the arrangement of FIG. 14, a suitable program would be contained in the RAM to operate the microcomputer or computer in order to generate the transformation curve of FIG. 12. Also, as will be seen hereinafter, the same components forming arrangement 64' with still another program serves as an actual working embodiment for the technique to be described hereinafter with regard to FIGS. 22-25.

The foregoing discussion in conjunction with FIGS. 15-21A, B has related to a technique for monitoring a patient's diastolic, systolic and mean pressures over an extended period of time by taking successive measurements at closely spaced intervals throughout the period and without having to subject the patient to high cuff pressures (on the order of his systolic pressure), except initially during a parameter determining cycle. The following technique to be described below in conjunction with FIGS. 22-25 does not require even one high pressure cycle. More specifically, the following is a technique for obtaining a patient's diastolic, mean and systolic pressures without ever having to subject the patient to cuff pressures on the order of his systolic pressure. In order to understand how this technique is achieved, attention is redirected to the previously described Link U.S. Pat. No. 3,903,872. It may be recalled from this patent and particularly the discussions associated with FIG. 5 thereof as well as the discussions provided herein that the actual blood pressure of a given patient at any point along the patient's actual blood pressure curve can be determined by measuring $\dot{p}$ at that time as the patient is subjected to different cuff pressures.

In the case of the present technique, the patient is subjected to cuff pressures only somewhat greater than the anticipated diastolic pressure of the patient and, in any event, pressures which are less than the patient's systolic pressure. The up-ramp cycle of FIG. 15c is illustrative of such pressures. Note that the patient during this cycle is subjected to at most about 120 Torr.

In accordance with this technique, it is first necessary to select two points in time $t_1$ and $t_2$ on the diastolic decline of the patient's actual blood pressure waveform. Once these points in time are selected, the patient's blood pressure cuff is varied through a range of pressures below the anticipated systolic pressure of the patient but including levels above and below the anticipated blood pressures of the patient at the selected points in time $t_1$ and $t_2$ on his actual waveform, thereby producing cuff pulses at these different pressure levels. The closer the selected times $t^1$ and $t_2$ are to the diastolic point in time on the patient's waveform, the lower the maximum cuff pressure need be. On the other hand the closer $t_1$ and $t_2$ are together the larger will be the errors resulting from the present technique (the subtraction of two large numbers). Because of the conflicting requirements above, a choice of $t_1$ near diastolic and of $t_2$ about half way toward systolic is reasonable. Thus, if the actual anticipated blood pressure at time $t_1$ is near the diastolic point in the waveform and if the anticipated pressure at $t_2$ is about midway between systolic and diastolic pressure, it would be necessary only to subject the patient to cuff pressures slightly greater than midway between systolic and diastolic pressure. In any event, once these points in time are selected and the patient is subjected to these cuff pressures, the two curves 64 and 66 illustrated in FIG. 22 can be generated. The solid line curve corresponds to $\dot{P}$ at the time $t_1$ and the dotted line curve corresponds to $\dot{P}$ at $t_2$. Actually, $t_1$ is the temporal center for the band $\Delta t_1$ illustrated in FIG. 23 and $t_2$ is the temporal center for the band $\Delta t_1$ in FIG. 23. The maximum value for each of these curves determines the patient's actual blood pressure at the associated time $t_1$ or $T_2$. Thus, in FIG. 22, it can be seen that the patient's blood pressure at the time $t_1$ in his waveform is 80 Torr (indicated at $D_1$) and the pressure at time $t_2$ is 100 Torr ($D_2$).

FIG. 23 diagrammatically illustrates the patient's transformation curve in association with his actual blood pressure pulses in order to illustrate the relationship between time $t_1$ and its associated band $\Delta t_1$. Note that the band is located within the diastolic decline of the actual blood pressure pulse. As the patient is subjected to increasing cuff pressures, the resultant time derivative of the measured cuff pulse ($\dot{P}$) first increases and then decreases, thereby resulting in the curve 64 of FIG. 22. This would also be true for $t_2$ and $\Delta t_2$ resulting in curve 66 of FIG. 22, where $\Delta t_2$ is shown up from $\Delta t_2$ is shown up from $\Delta t_1$ on the diastolic decline.

Once either of the curves in FIG. 22 is generated, for example curve 64, it can be integrated to provide the patient's transformation curve which is generally indicated by the reference numeral 80 in in FIGS. 23 and 24. This curve is placed in the coordinate system shown such that the vertical axis at zero transmural pressure extends through the center of its maximum slope for the reasons to be discussed below and such that the horizontal axis is located near the bottom of the curve, although this is not critical. Note that the horizontal or transmural pressure axis corresponds to $P_w$ which is equal to the actual blood pressure $P_b$ minus the applied cuff pressure $P_c(dc)$. Also note that the patient was subjected to a maximum cuff pressure of 120 Torr and therefore the horizontal axis of the transformation curve goes a limited distance to the left of the vertical axis depending on the patient's diastolic pressure. Nevertheless, it is not necessary to go any further to the left for purposes of the present technique, as will be seen.

The transformation curve 80 is obtained by integrating over curve 64 according to the procedures described above. The vertical axis at 80 Torr for curve 64 becomes the zero axis for curve 80. The corresponding values are shown in FIG. 23. Thus, keeping the definition $P_2 = P_b - P_c(dc)$ in mind, when $P_b$ is minimum (at 80 Torr) and $P_c(dc)$ is equal to 80 Torr, $P_2 = 0$; when $P_c(dc) = 10$ Torr then $P_w = 70$ Torr and so on. Having generated the transformation curve 80 in FIGS. 23 and 24, attention is now directed to the way in which the patient's diastolic and systolic pressures are determined using this curve in combination with the pressures values $D_1$ and $D_2$ determined by means of the curves illustrated in FIG. 22. At the outset, it is necessary to select one of the cuff pulses $P_c(ac)$ generated in order to provide the curves of FIG. 22. Any such pulse will do, for example the cuff pulse produced at a cuff pressure of 60 Torr. The pressure points $D_1$ and $D_2$ are located on this cuff pulse by locating the times $t_1$ and $t_2$. This can be done by moving back from the diastolic end of the cuff pulse the appropriate amount of time. This cuff pulse including the pressure points $D_1$ and $D_2$ is illustrated in FIG. 24 at 81. At the same time, the $D_1$ and $D_2$ points are located on the horizontal $P_w$ axis of the transformation curve for a cuff pressure of 60 Torr. Since $D_1$ equals 80 Torr, the point on the horizontal $P_w$ axis corresponding to this point is 20 Torr (80 Torr minus 60 Torr). Since $D_2$ equals 100 Torr, the $D_2$ point on the horizontal $P_w$ axis is 40 Torr (100 Torr minus 60 Torr).

Once the $D_1$ and $D_2$ points are located on the horizontal axis of the transformation curve, vertical lines 82 and 84 are drawn upwardly from these points until they intersect the transformation curve. Horizontal lines 86 and 88 are then drawn from these intersecting points to the left, as illustrated. At the same time, vertical lines 90 and 92 are drawn from the points $D_1$ and $D_2$ on the cuff pulse 81 illustrated in FIG. 24 until they intersect lines 86 and 88 respectively at the two points $D_1'$ and $D_2'$ respectively as seen in FIG. 24. The entire cuff pulse 81 can then be scaled to match points $D_1'$ and $D_2'$ as indicated by means of the dotted lines to provide the appropriately scaled reproduction pulse 81'. In other words, each section of the reproduced cuff pulse 81' in FIG. 24 is proportionate to the corresponding section of the original cuff pulse 81 but scaled to match the points $D_1'$ and $D_2'$.

From the base of the scaled cuff pulse 81'; the diastolic pressure of the patient can be determined by finding the point of intersection of the transformation curve 80 with the horizontal line 100. From this intersecting point, the vertical line 102 is drawn downward until it intersects the horizontal $P_w$ axis of the transformation curve. It does so at a transmural pressure $(P_w)$ of 10 Torr. Therefore, the diastolic pressure is equal to 70 Torr (10 Torr plus 60 Torr where $P_b = P_w + P_c(dc)$). The same procedure may be used to determine the patient's systolic pressure. More specifically, a horizontal line 104 is drawn from the top of the scaled pulse to an intersecting point of the transformation curve, at which point the vertically downward line 106 is drawn until it intersects the horizontal axis of the transformation curve. It does so at 60 Torr. Therefore, the systolic pressure is equal to 120 Torr (60 Torr plus 60 Torr).

The foregoing procedure could be repeated for cuff pulses at different applied cuff pressures and the results could be averaged to obtain averaged values for the systolic and diastolic pressures. Moreover, $D_1$ could be selected at a time $t_1$ sufficiently close to the patient's diastolic pressure so that $D_1$ automatically provides the patient's diastolic pressure and it is mainly necessary to carry out the foregoing procedure to provide the systolic pressure. Moreover, this procedure can be repeated successively over a period of time in order to monitor the patient's diastolic and systolic blood pressures over a period of time without ever subjecting the patient to cuff pressures much greater than midway between the patient's systolic and diastolic pressures.

The entire pulse 81' can now be transformed through the transformation curve 80 to obtain the transformed blood pressure pulse 81" shown in dot-dash fashion in FIG. 24. Every pressure on the transformed blood pressure pulse 81" is now known and the mean blood pressure can now be calculated by integration and the entire waveform 81" can be presented on a suitable monitor. For added accuracy additional points $D_3$, $D_4$–$D_n$ can be included on curve 81 by an analysis identical to the above.

Referring to FIG. 25, attention is now directed to an overall apparatus 110 for carrying out the technique described with regard to FIGS. 22–24. This apparatus includes a blood pressure cuff or pad 112 positioned adjacent a suitable artery of the patient. Means generally indicated at 114 are provided for placing the cuff at different pressure levels below the anticipated systolic pressure of the patient but including levels above and below the anticipated pressure of the patient at the selected points in time $t_1$ and $t_2$ on his actual waveform. Circuitry generally indicated at 116 is provided for producing cuff pulses at these different pressure levels. These cuff pulses are input to circuitry 118 which responds thereto for producing the pressure values at $D_1$ and $D_2$ and at the same time this circuitry generates the curves of FIG. 22. One of these curves is input to circuitry 120 which integrates the curve and provides the transformation curve 80 as a result thereof. Finally, circuitry 122 utilizes this transformation curve, the pressures $D_1$ and $D_2$ and at least one of the cuff pulses (for example cuff pulse 81) to (1) establish the positional relationship between the transformation curve and selected cuff pulse and (2) the correct scaling of the latter relative to the transformation curve (thereby producing reproduction pulse 81'). Thereafter, circuitry 122 uses the correctly scaled reproduced cuff pulse 81' and its positional relationship with regard to the transformation curve to determine the systolic pressure of the patient and his diastolic pressure, if the latter is not the blood pressures $D_1$ or $D_2$.

The discussion immediately above has been a functional description of an arrangement 110 for carrying out the technique associated with FIGS. 22–24. In a preferred embodiment, this is carried out by means of the components making up the block diagram illustrated in FIG. 21b. The cuff or pressure pad 66' in combination with pump and pneumatic control 68', pressure transducer 69' and amplifier and band pass filter 70' together provide cuff pulses as the patient is subject to the up-ramp cycle of FIG. 15c. The analog MUX and the A/D converter 71' and 72' digitizes this information and inputs it to the microcomputer or computer 73'. A suitable program in ROM 74' operates the microcomputer or computer so as to produce the curves 64 and 66 of FIG. 22, it determines the pressures at $D_1$ and $D_2$ and it generates the transformation curve 80, then carries out the steps associated with FIG. 24 in order to obtain the patient's diastolic and systolic pressure and also the patient's full blood pressure waveform (the waveform 81" in FIG. 24).

In the last mentioned technique the points $D_1$ and $D_2$ were selected to lie on the diastolic decline of the blood pressure waveform. However, it should be apparent that points $D_1$ and $D_2$ can be located at any two points on the blood pressure waveform provided that the blood pressure difference between the two points is reasonably large. Specifically the two points can be chosen on the systolic rise part of the waveform between the diastolic end point of the previous pulse and the systolic peak of the current pulse. All the descriptions of this last mentioned technique hold true for these two points except that the polarity of the differential quantities $\Delta V$ and $\Delta P_c(ac)$ reverses.

In this latter technique described with respect to FIGS. 22-24, the patient was subjected to cuff pressures between the diastolic and systolic pressures as contrasted with pressures well above systolic when using prior art techniques. This resulted in the advantage of decreasing the discomfort to the patient due to the subjected cuff pressures, as compared to those techniques which require higher pressures. As an additional advantage, the present technique is more accurate at all pressure ranges. This is because the lower cuff pressures do not fully collapse the artery being monitored, even at the highest cuff pressures (e.g. 120 Torr). An open artery has more sensitivity to the blood pressure within than a collapsed artery. Furthermore, the frequency response of an open artery is certainly higher than a collapsed artery. In the case of battery operated instruments a further advantage resides in the reduction in consumption of energy by the air pump used to pressurize the pressure cuff or pad. Thus, the present technique combines improved patient comfort, improved accuracy and the need for less power.

Turning now to FIG. 26, there is shown a flow diagram corresponding to the procedure described previously with respect to FIGS. 6-10 and incorporating the various steps carried out by the computer forming part of the block diagram illustrated in FIG. 21B. Before proceeding with a description of this flow diagram, it should be noted that the term "Pc" therein refers to the combination of cuff pressure $Pc(dc)$ and cuff pulses $Pc(ac)$ and that the $\dot{P}c$ refers to the derivative of $Pc$ and therefor the sum of the derivative of the cuff pressure $\dot{P}c(dc)$ plus the derivative of the cuff pulses $\dot{P}c(ac)$. It should be further noted that the derivative of the cuff pulses $\dot{P}c(dc)$ corresponds to the ramp gradient characteristic resulting from the way in which the blood pressure cuff is pressurized. More specifically, as each cuff pulse $Pc(ac)$ is generated at a given cuff pressure $Pc(dc)$ it is done at continuously greater or lesser cuff pressures which form a continuously upwardly extending or downwardly extending ramp.

As will be seen below, the first ten steps (boxes) and box 19 in the flow diagram of FIG. 26 serve to receive physical cuff pressures from the cuff and these cuff pressures are converted to electrical analog signals and then digital signals and eventually the ramp component or gradient of the overall signal which is signal $\dot{P}c$ is eliminated so as to provide the cuff pulses $Pc(ac)$ by themselves on a horizontal axis rather than along a ramp gradient. At the same time, the overall signal $Pc$ and the cuff pulses $Pc(ac)$ are differentiated.

Referring now specifically to the flow diagram of FIG. 26, step one begins after the start button is depressed and corresponds to pressurizing the cuff at different upwardly ramping or downwardly ramping cuff pressures $Pc(dc)$. In step two the transducer forming part of the overall system receives the cuff pressures and converts them to analog signals which are filtered for 60 hz and noise (step three). These signals $\dot{P}c$ are then differentiated by box four and the differentiated components $\dot{P}c(ac)$ and $\dot{P}c(dc)$ are alternately fed to an analog/digital converter (box six) by means of the multiplexor corresponding to box five. Both $Pc$ and $\dot{P}c$ are stored in RAM as represented by box seven. As this is done, the system as represented by box eight continuously searches for the beginning of the cuff pulse by specifically looking for the beginning of its systolic rise. When that is found, $\dot{P}c$ is averaged (integrated) over a full pulse and therefore corresponds to $Pc(dc)$ or the ramp gradient. Finally, as indicated in box ten, $\dot{P}c(dc)$ is subtracted from $\dot{P}c$ leaving $\dot{P}c(ac)$ which is the differential without the ramp gradient. Box nineteen integrates $\dot{P}c(ac)$ with respect to time to provide the cuff pulses by themselves, that is, without the ramp gradient. These separated cuff pulses and both $Pc$ and $\dot{P}c$ are stored in RAM.

Continuing on with the flow diagram, steps eleven through thirteen use the systolic rise (step eight) to establish the various previously described times $t_1, t_2 \ldots t_n$. Steps fourteen through eighteen establish and store $Pc(ac)$ for $t_1$, $T_2$ and so on at each cuff pressure $Pc(dc)$ and establish the maximum for $\dot{P}c(ac)$ for each cuff pulse. This, in turn, corresponds to the previously described points $Pb1$, $Pb2 \ldots$ through $Pbn$. These points are sufficient to generate the desired approximated waveform. However, as indicated previously, there are certain points which cannot be differentiated including specifically the systolic point and the maximum and minimum points on the dichrotic notch, as indicated in the flow diagram. Therefore, the remaining steps in the flow diagram establish the systolic pressure in order to terminate the process and display the appropriate information.

Turning now to FIG. 27, there is shown a flow diagram corresponding to the procedure described previously with respect to FIGS. 11-14 and incorporating the various steps carried out by the computer forming part of the block diagram illustrated in FIG. 21B. Before proceeding with a description of this flow diagram, it should be noted that the term "Pc" therein refers to the combination of cuff pressure $Pc(dc)$ and cuff pulses $Pc(ac)$ and that the $\dot{P}c$ refers to the derivative of $Pc$ and therefor the sum of the derivative of the cuff pressure $\dot{P}c(dc)$ plus the derivative of the cuff pulses $\dot{P}c(ac)$. It should be further noted that the derivative of the cuff pulses $\dot{P}c(dc)$ corresponds to the ramp gradient characteristic resulting from the way in which the blood pressure cuff is pressurized. More specifically, as each cuff pulse $Pc(ac)$ is generated at a given cuff pressure $Pc(dc)$ it is done at continuously greater or lesser cuff pressures which form a continuously upwardly extending or downwardly extending ramp.

The first ten steps (boxes) and box 14 in the flow diagram of FIG. 27 correspond to boxes 1-10 and 19 in the flow diagram of FIG. 26 and reference is made thereto. Having described the function of these boxes above attention is now directed to the way in which the transformation curve is generated using solely the subjects diastolic and systolic pressure and curve 40 in FIG. 11. Note that the various peak to peak amplitudes A correspond to the amplitudes of signals $Pc(ac)$ which are stored in ROM along with their corresponding cuff pressures $Pc(dc)$. Note also that the flow diagram provides steps or boxes to determine the subjects diastolic pressure and systolic pressure. Once this is done, the band $\Delta P$ utilized in generating the transformation curve can be established and using all of this information, the curve of FIG. 12 can be constructed, as indicated in the flow diagram.

Turning now to FIG. 28A, there is shown a flow diagram corresponding to the procedure described previously with respect to FIGS. 15-21A and incorporating the various steps carried out by the computer forming part of the block diagram illustrated in FIG. 21B. Before proceeding with a description of this flow diagram, it should be noted that the term "Pc" therein refers to the combination of cuff pressure $Pc(dc)$ and cuff pulses Pc(ac) and that the Ṗc refers to the derivative of Pc and therefor the sum of the derivative of the cuff pressure Ṗc(dc) plus the derivative of the cuff pulses Ṗc(ac). It should be further noted that the derivative of the cuff pulses Ṗc(dc) corresponds to the ramp gradient characteristic resulting from the way in which the blood pressure cuff is pressurized. More specifically, as each cuff pulse Pc(ac) is generated at a given cuff pressure Pc(dc) it is done at continuously greater or lesser cuff pressures which form a continuously upwardly extending or downwardly extending ramp.

The first ten steps (boxes) and box 14 in the flow diagram of FIG. 28A correspond to Boxes 1-10 and 19 in the flow diagram of FIG. 26 and reference is made thereto. The remaining steps (boxes) show and indicate the steps involved in carrying out the procedures described in the specification with respect to the stat mode embodiment associated with FIGS. 15-21A and 25.

Turning now to FIG. 28B, there is shown a flow diagram corresponding to the procedure described previously with respect to FIGS. 22-25 and incorporating the various steps carried out by the computer forming part of the block diagram illustrated in FIG. 21B. Before proceeding with a description of this flow diagram, it should be noted that the term "Pc" therein refers to the combination of cuff pressure Pc(dc) and cuff pulses Pc(ac) and that the Ṗc refers to the derivative of Pc and therefor the sum of the derivative of the cuff pressure Ṗc(dc) plus the derivative of the cuff pulses Ṗc(ac). It should be further noted that the derivative of the cuff pulses Ṗc(dc) corresponds to the ramp gradient characteristic resulting from the way in which the blood pressure cuff is pressurized. More specifically, as each cuff pulse Pc(ac) is generated at a given cuff pressure Pc(dc) it is done at continuously greater or lesser cuff pressures which form a continuously upwardly extending or downwardly extending ramp.

The first ten steps (boxes) and box 14 in the flow diagram of FIG. 28B correspond to Boxes 1-10 and 19 in the flow diagram of FIG. 26 and reference is made thereto. The remaining steps (boxes) show and indicate the steps involved in carrying out the procedures described in the specification with respect to the stat mode embodiment associated with FIGS. 22-25.

What is claimed is:

1. A method of providing an arterial curve characteristic of a particular mammal, comprising the steps of:
   (a) placing a blood pressure cuff around a particular artery of said mammal;
   (b) using means cooperating with said cuff, pressurizing the latter at a number of different pressure levels from zero pressure to a pressure at least equal to the mammal's systolic pressure and generating cuff pulses having peak to peak amplitude values corresponding to and dependent on said different pressure levels;
   (c) determining the diastolic and systolic pressures of said mammal; and
   (d) graphically generating said arterial curve in a way which requires the use of said peak to peak values and said diastolic and systolic pressures.

2. A method according to claim 1 wherein only said peak to peak amplitude values and said diastolic and systolic pressures are used to graphically generate said arterial curve.

3. An apparatus for providing an arterial curve characteristic of a particular mammal, comprising:
   (a) a blood pressure cuff for placement around a particular artery of said mammal;
   (b) means cooperating with said cuff for pressurizing the latter at a number of different pressure levels from zero pressure to a pressure at least equal to the mammal's systolic pressure and for generating cuff pulses having peak to peak amplitude values corresponding to and dependent on said different pressure levels;
   (c) means for determining the diastolic and systolic pressures of said mammal; and
   (d) means for graphically generating said arterial curve in a way which requires the use of said peak to peak values and said diastolic and systolic pressures.

4. An apparatus according to claim 3 wherein only said peak to peak amplitude values and said diastolic and systolic pressures are used to graphically generate said arterial curve.

5. A method of providing an arterial curve characteristic of a particular mammal, comprising the steps of:
   (a) placing a cuff or cuff-like member adjacent a particular artery of said mammal;
   (b) using means cooperating with said cuff or cuff-like member, pressurizing the latter at a number of different pressure levels from zero pressure to a pressure at least equal to the mammal's systolic pressure and generating cuff pulses having peak to peak amplitude values corresponding to and dependent on said different pressure levels;
   (c) determining the diastolic and systolic pressure of said mammal; and
   (d) generating said arterial curve in a way which requires the use of said peak to peak values and said diastolic and systolic pressures.

6. A method according to claim 5 wherein only said peak to peak amplitude values and said diastolic and systolic pressures are used to generate said arterial curve.

7. An apparatus for providing an arterial curve characteristic of a particular mammal, comprising:
   (a) blood pressure cuff means for placement adjacent a particular artery of said mammal;
   (b) means cooperating with said cuff means for pressurizing the latter at a number of different pressure levels from zero pressure to a pressure at least equal to the mammal's systolic pressure and for generating cuff pulses having peak to peak amplitude values corresponding to and dependent on said different pressure levels;
   (c) means for determining the diastolic and systolic pressures of said mammal; and
   (d) means for generating said arterial curve in a way which requires the use of said peak to peak values and said diastolic and systolic pressures.

8. An apparatus according to claim 7 wherein only said peak to peak amplitude values and said diastolic and systolic pressures are used to generate said arterial curve.

9. A method of providing an arterial curve characteristic of a particular mammal where one axis of the curve in a given coordinate system represents the volume of a particular artery segment of the mammal and a second axis normal to said one axis represents the wall pressure of said artery segment, comprising the steps of:
   (a) placing a cuff or cuff-like member adjacent said particular artery segment of said mammal;

(b) using means cooperating with said cuff or cuff-like member, pressurizing the latter at a number of different pressure levels from zero pressure to a pressure at least equal to the mammal's systolic pressure and generating cuff pulses having peak to peak amplitude values corresponding to and dependent on said different pressure levels;

(c) determining the diastolic and systolic pressure of said mammal; and (d) generating said arterial curve in a way which requires the use of said peak to peak values and said diastolic and systolic pressures.

10. An apparatus for providing an arterial curve characteristic of a particular mammal where one axis of the curve in a given coordinate system represents the volume of a particular artery segment of the mammal and a second axis normal to said one axis represents the wall pressure of said artery segment, comprising:

(a) a blood pressure cuff means for placement adjacent said segment of said mammal;

(b) means cooperating with said cuff means for pressurizing the latter at a number of different pressure levels form zero pressure to a pressure at least equal to the mammal's systolic pressure and for generating cuff pulses having peak to peak amplitude values corresponding to and dependent on said different pressure levels;

(c) means for determining the diastolic and systolic pressures of said mammal; and (d) means for generating said arterial curve in a way which requires the use of said peak to peak values and said diastolic and systolic pressures.

* * * * *